US010697959B2

(12) United States Patent
Kaneko et al.

(10) Patent No.: US 10,697,959 B2
(45) Date of Patent: Jun. 30, 2020

(54) SANDWICH ASSAY USING LABELED LECTIN AND KIT THEREFOR

(71) Applicant: Konica Minolta, Inc., Tokyo (JP)

(72) Inventors: Tomonori Kaneko, Hachioji (JP); Takatoshi Kaya, Inagi (JP)

(73) Assignee: KONICA MINOLTA, INC., Tokyo (JP)

(*) Notice: Subject to any disclaimer, the term of this patent is extended or adjusted under 35 U.S.C. 154(b) by 164 days.

(21) Appl. No.: 15/320,118

(22) PCT Filed: Jun. 1, 2015

(86) PCT No.: PCT/JP2015/065731
§ 371 (c)(1),
(2) Date: Dec. 19, 2016

(87) PCT Pub. No.: WO2015/194350
PCT Pub. Date: Dec. 23, 2015

(65) Prior Publication Data
US 2017/0122940 A1 May 4, 2017

(30) Foreign Application Priority Data
Jun. 20, 2014 (JP) ................. 2014-127372

(51) Int. Cl.
G01N 33/543 (2006.01)
(52) U.S. Cl.
CPC ... *G01N 33/54393* (2013.01); *G01N 2333/42* (2013.01); *G01N 2333/4724* (2013.01);
(Continued)
(58) Field of Classification Search
CPC .................................................. G01N 33/543
See application file for complete search history.

(56) References Cited

U.S. PATENT DOCUMENTS 9,874,558 B2 * 1/2018 Isoda ................. G01N 33/50
2015/0140571 A1 * 5/2015 Kaneko ............. G01N 33/5308
435/7.1

FOREIGN PATENT DOCUMENTS

| EP | 0399464 A2 | 11/1990 |
| JP | S61-292062 A | 12/1986 |
| JP | H3-73852 A | 3/1991 |
| JP | 2001-255325 A | 9/2001 |
| JP | 2006-112834 A | 4/2006 |
| JP | 2009-53195 A | 3/2009 |
| JP | 2010-60293 A | 3/2010 |
| JP | 2010-127827 A | 6/2010 |

(Continued)

OTHER PUBLICATIONS

Takeya et al., ("Presence of β-linked GalNAc residues on N-glycans of human thyroglobulin", Life Sciences, vol. 80, pp. 538-545, published 2007). (Year: 2007).*

(Continued)

Primary Examiner — Tracy Vivlemore
Assistant Examiner — Nam P Nguyen
(74) Attorney, Agent, or Firm — Lucas & Mercanti, LLP

(57) ABSTRACT

The present invention provides a sandwich assay for quantifying a glycoprotein, which is a substance to be detected, in a sample using a labeled lectin, wherein the effect attributed to a contaminant, namely noise on the quantified value of the substance to be detected, is suppressed by introduction of a simple treatment. The sandwich assay includes a treatment for inhibiting the binding of the labeled lectin to a sugar chain carried by the contaminant non-specifically adsorbed to the measurement region, which contaminant is contained in the sample and which sugar chain is the same as that of the substance to be detected.

5 Claims, 11 Drawing Sheets

(52) U.S. Cl.
CPC . *G01N 2333/4728* (2013.01); *G01N 2400/00* (2013.01); *G01N 2400/02* (2013.01); *G01N 2440/38* (2013.01)

(56) References Cited

FOREIGN PATENT DOCUMENTS

| JP | 2012-185172 A | 9/2012 |
|---|---|---|
| JP | 2013-076666 A | 4/2013 |
| JP | 2013-253866 A | 12/2013 |
| JP | 5413544 B1 | 2/2014 |
| WO | 2010/074265 A1 | 7/2010 |
| WO | 2010/090264 A1 | 8/2010 |
| WO | 2014/025013 A1 | 2/2014 |
| WO | 2014/087802 A1 | 6/2014 |

OTHER PUBLICATIONS

International Search Report dated Aug. 4, 2015 from corresponding International Application; International Application No. PCT/JP2015/065731; Total of 3 pages.

Written Opinion of the International Searching Authority dated Aug. 4, 2015 from corresponding International Application No. PCT/JP2015/065731; English translation of Written Opinion of the International Searching Authority; Total of 14 pages.

Sugar Chain s of Human Cord Serum a-Fetoprotein: Characteristics of N-linked Sugar Chains of Clycoproteins Produced in Human Live and Hepatocellular Carcinomas, K. Yamashita et al., Cancer Res., 53, 1 (1993).

Carbohydrate Structures of Nonspecific Cross-reacting Antigen-2, a Glycoprotein Purified from Meconium as an antigen Cross-reacting with Anticarcinoembryonic Antigen Antibody, K. Yamashita et al., The Journal of Biological Chemistry, 264, 17873 (1989).

Structural Studies of the Carbohydrate Moieties of Carcinoembryonic Antigens, K. Yamashita et al., Cancer Res., 47,3451 (1987).

Extended European Search Report dated Dec. 20, 2017 from the corresponding European Application No. 15809575.2.

Siu-Cheong Ho et al: "Carbohydrate binding activities of Bradyrhizobium japonicum III. Lectin expression, bacterial binding, and nodulation efficiency" The Plant Journal, vol. 5, No. 6, Jun. 1, 1994 pp. 873-884.

Notification of Reasons for Rejection dated Sep. 18, 2018 from the corresponding Japanese Patent Application No. JP 2016-529213 and English translation.

Office Action dated Sep. 5, 2018 from corresponding European Application No. EP 15809575.2.

* cited by examiner

[Fig. 1]
[A]
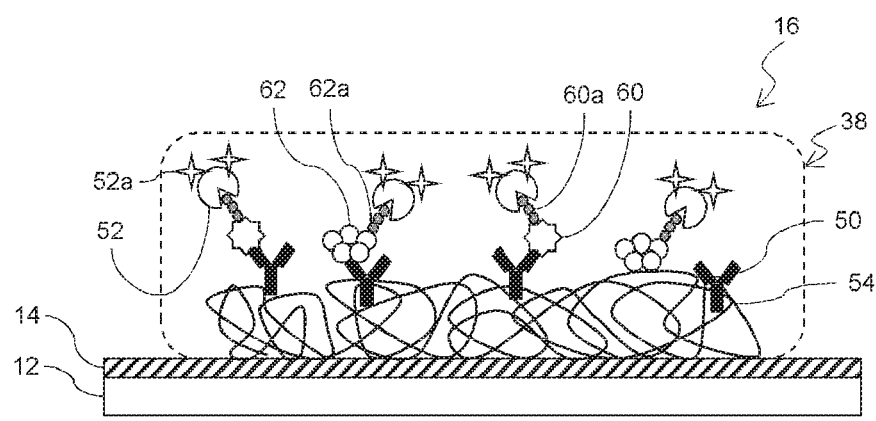
[B]
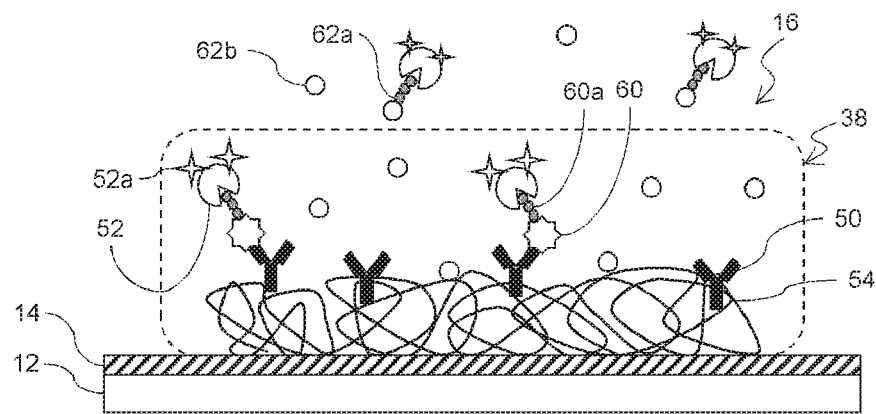

[Fig. 2]
[A]
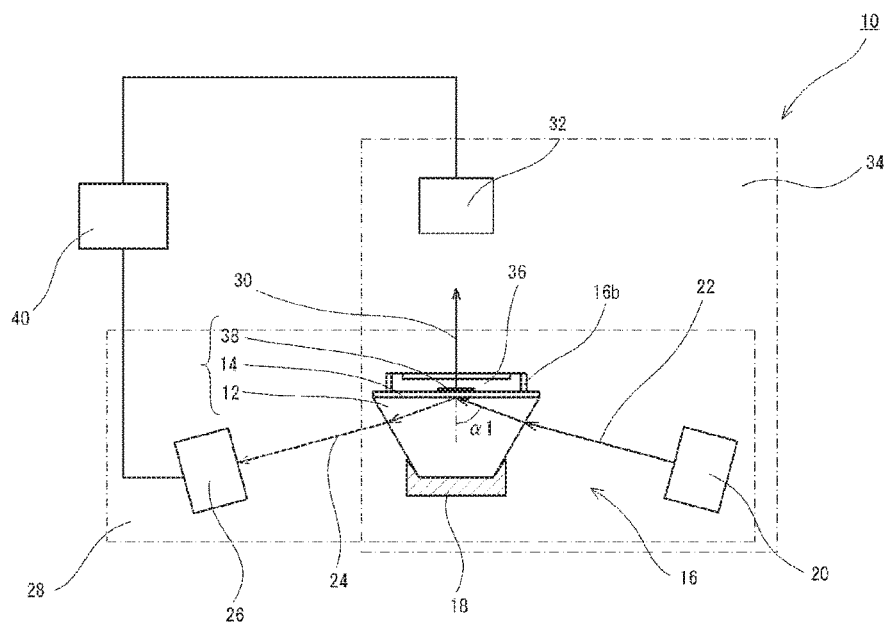
[B]
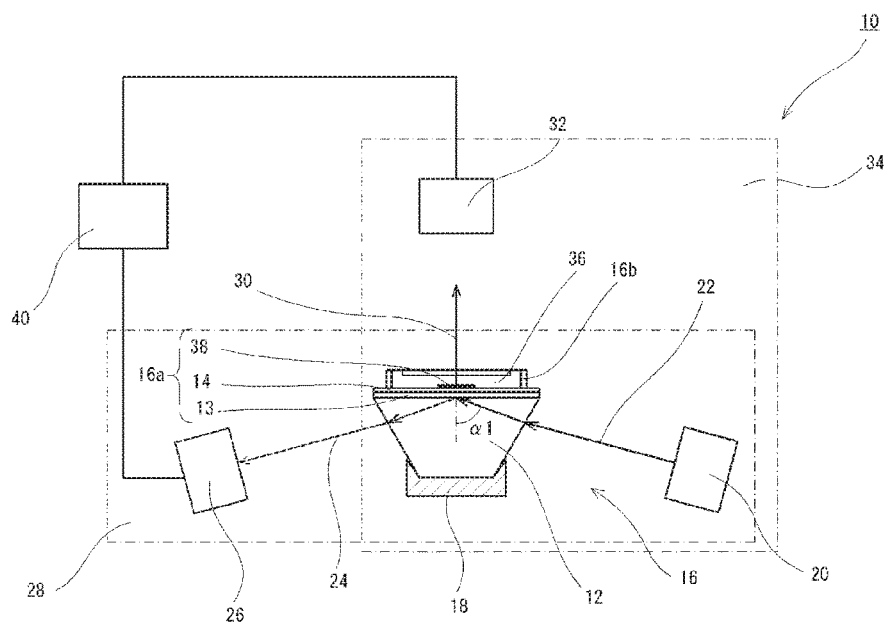

[Fig. 3]
[A]
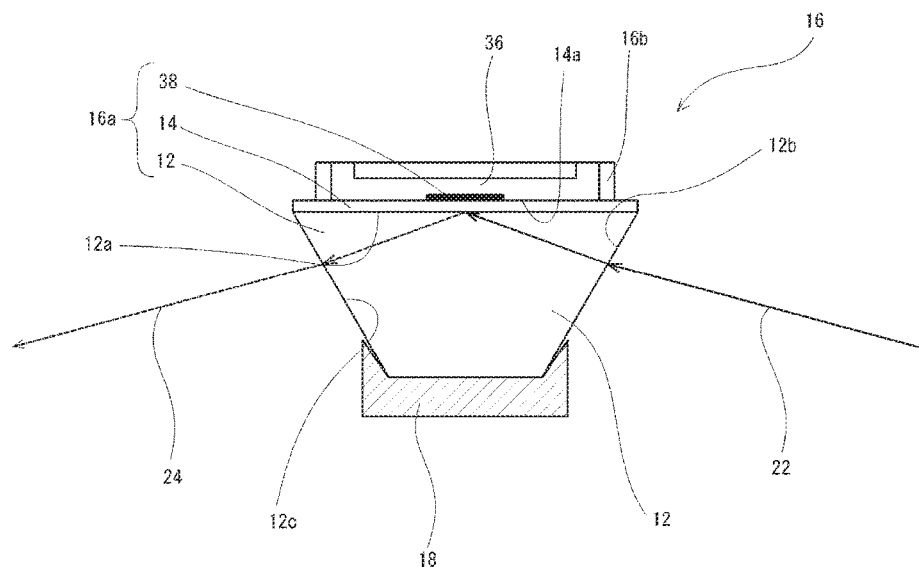
[B]
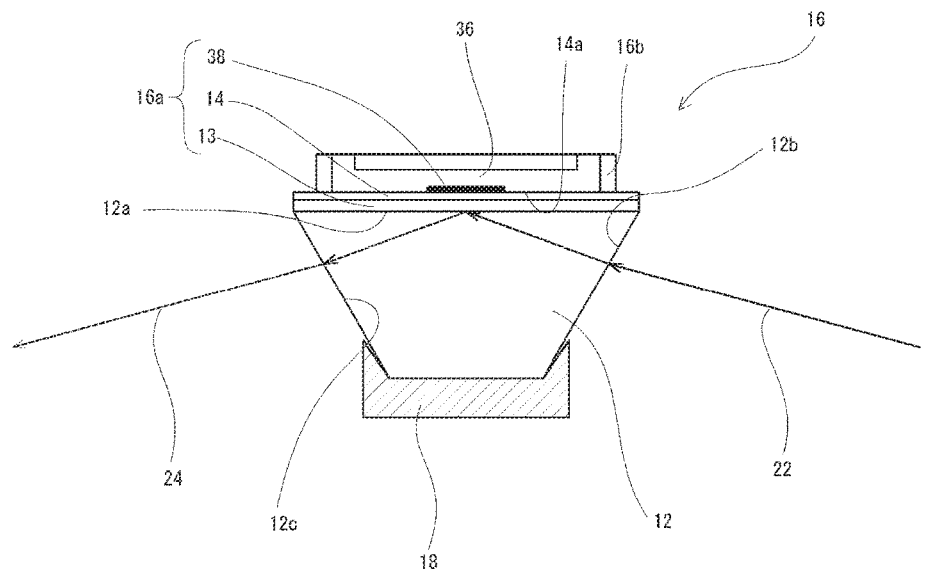

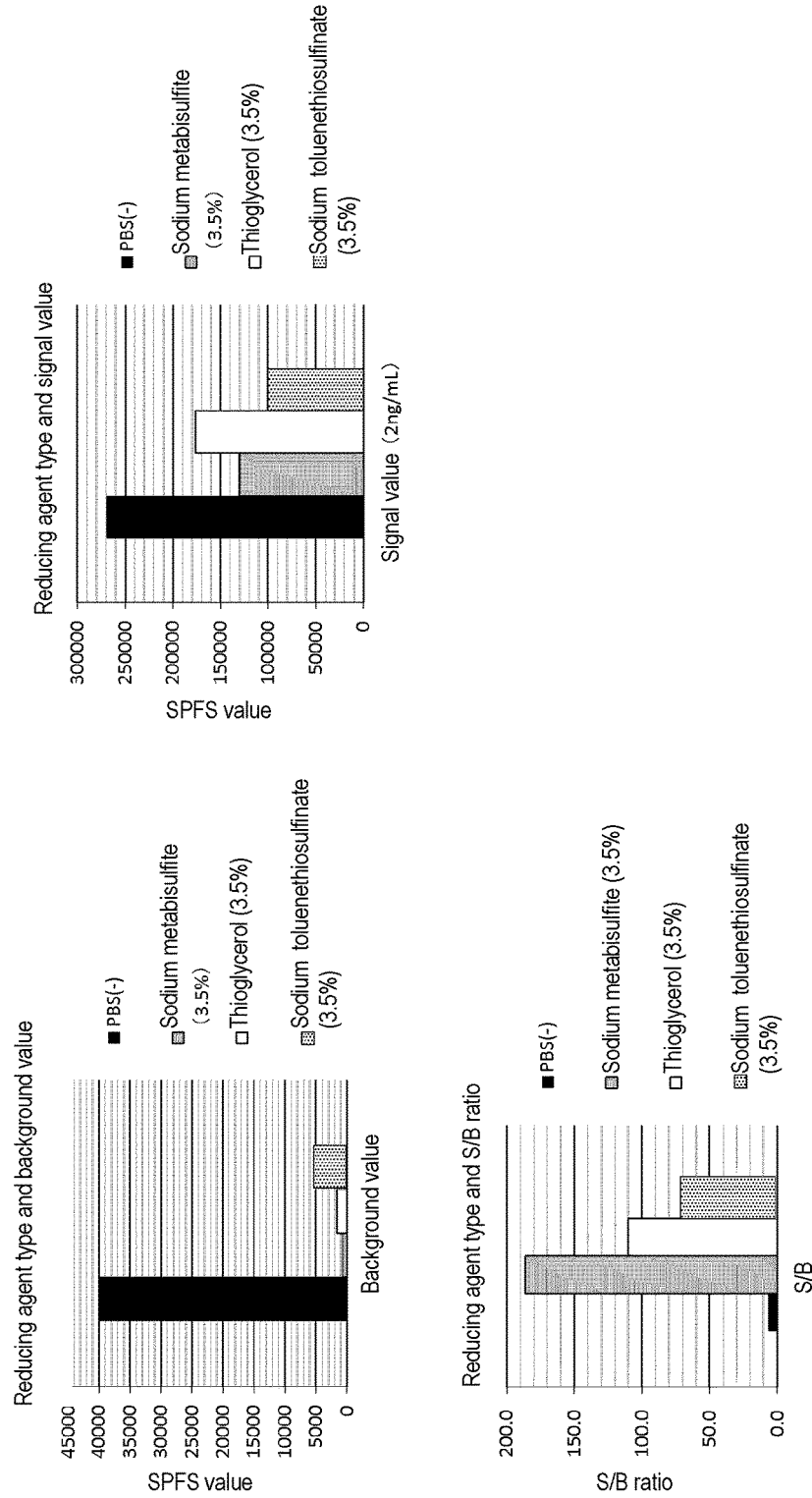
[Fig. 4]

[Fig. 5]
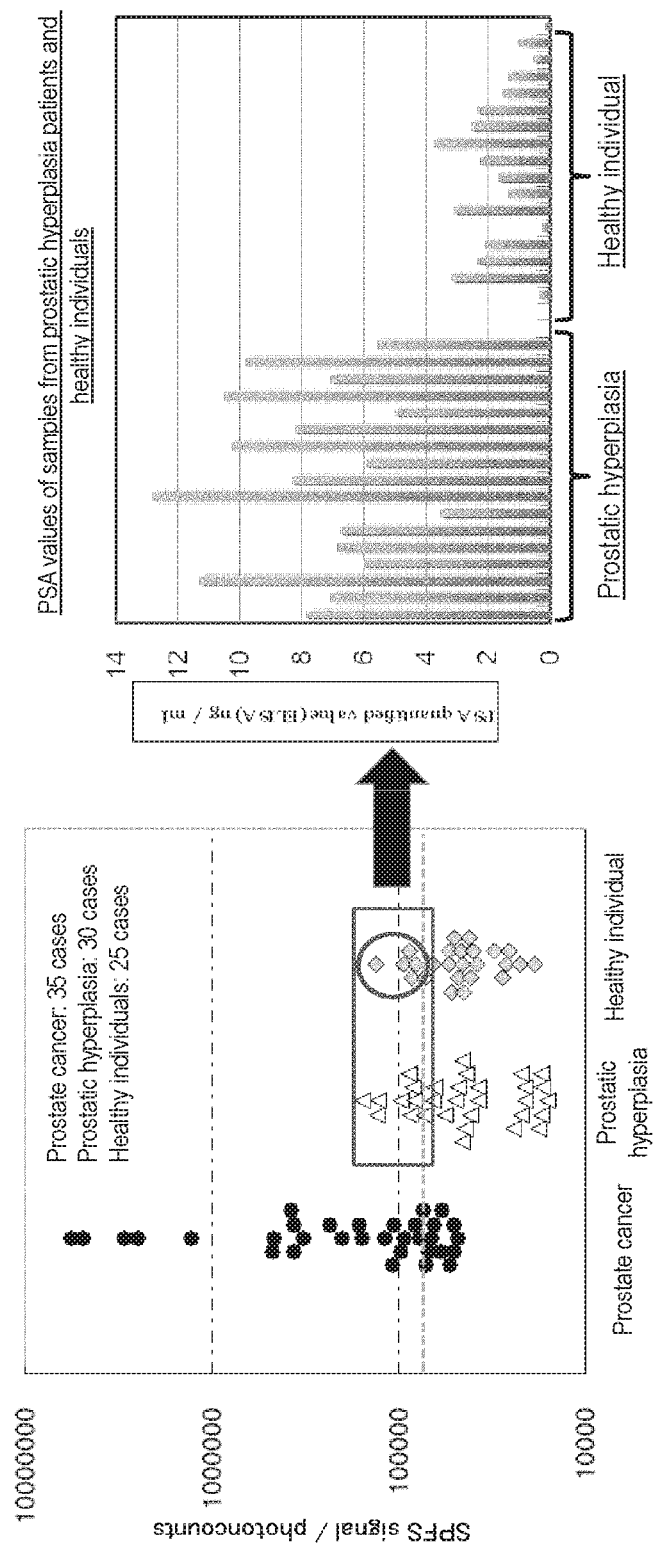

[Fig. 6]
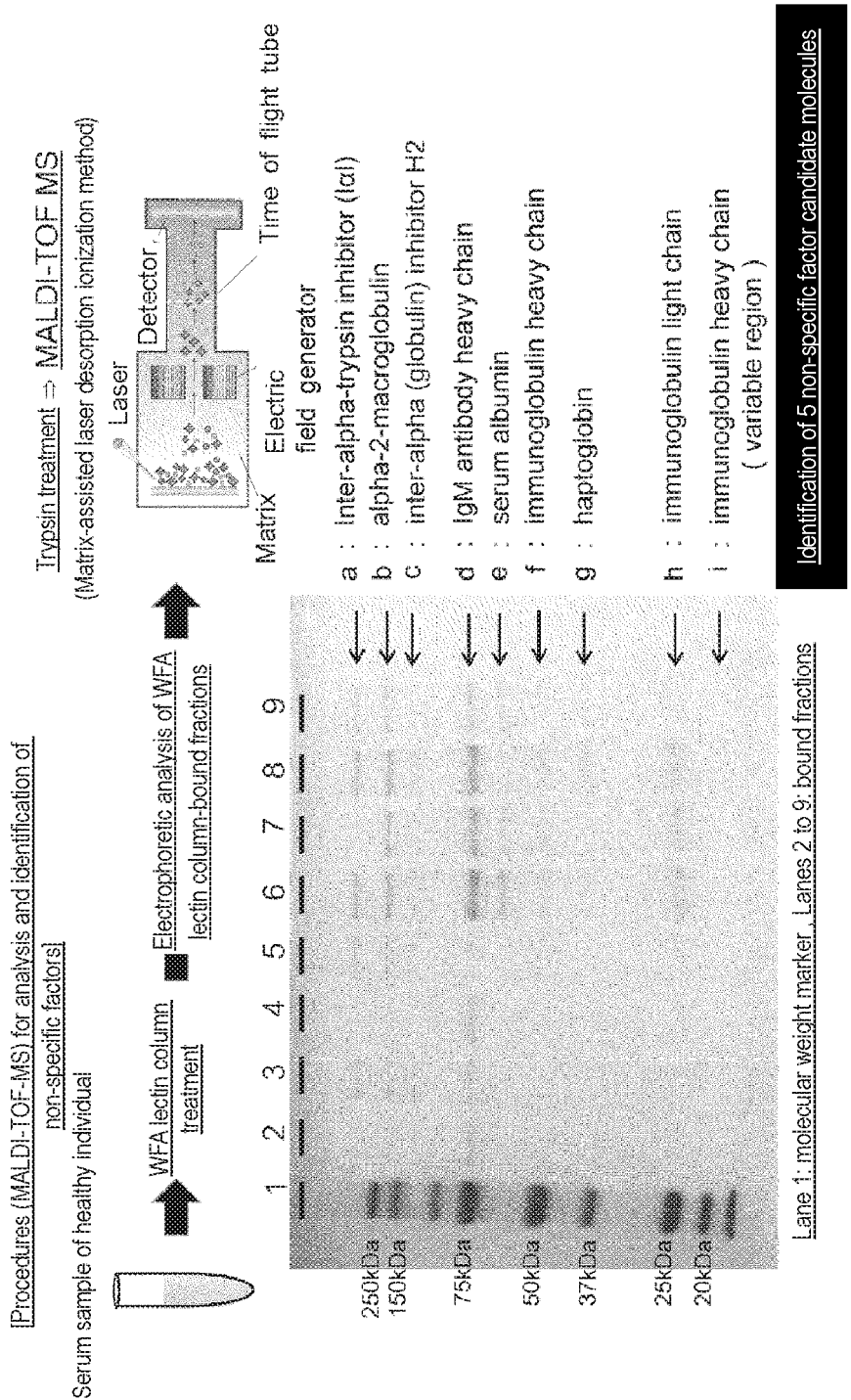

[Fig. 7]
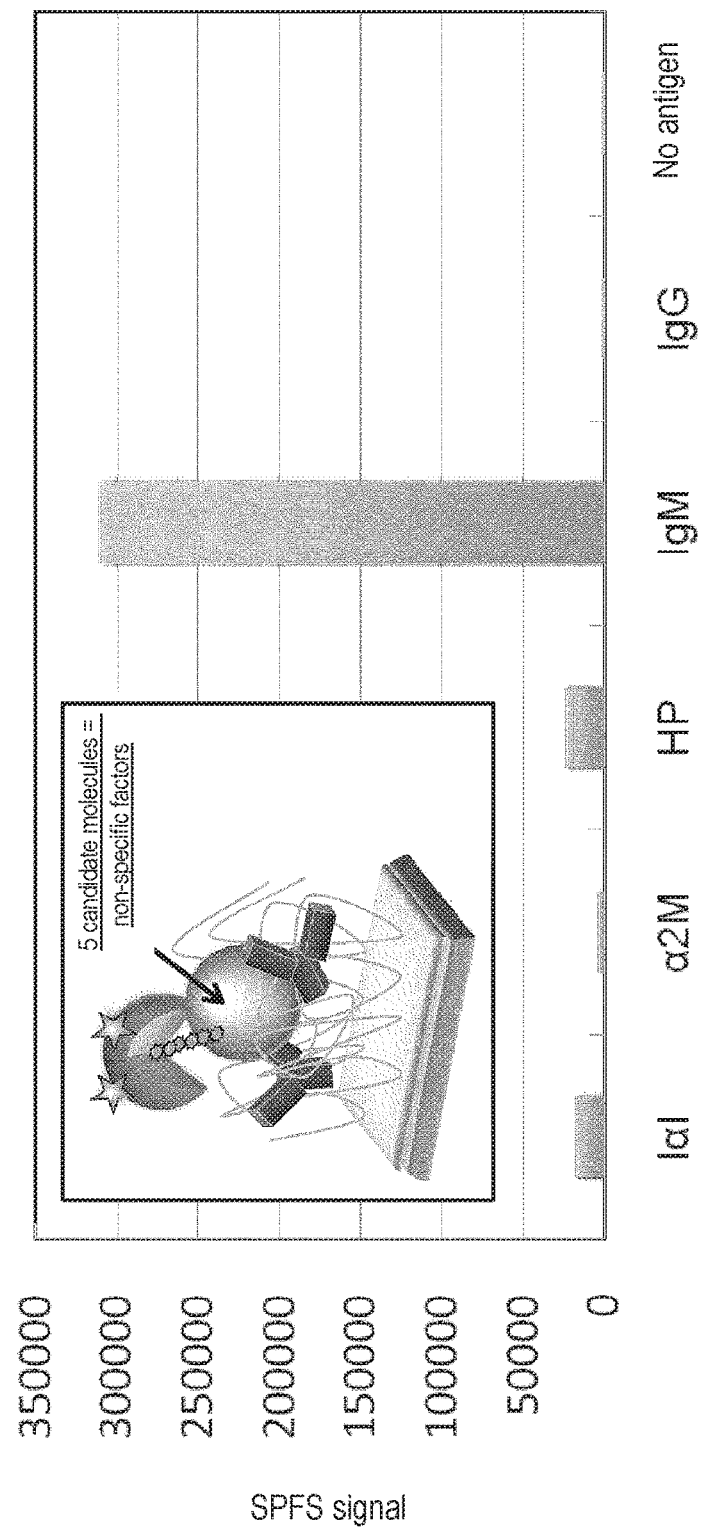

[Fig. 8]
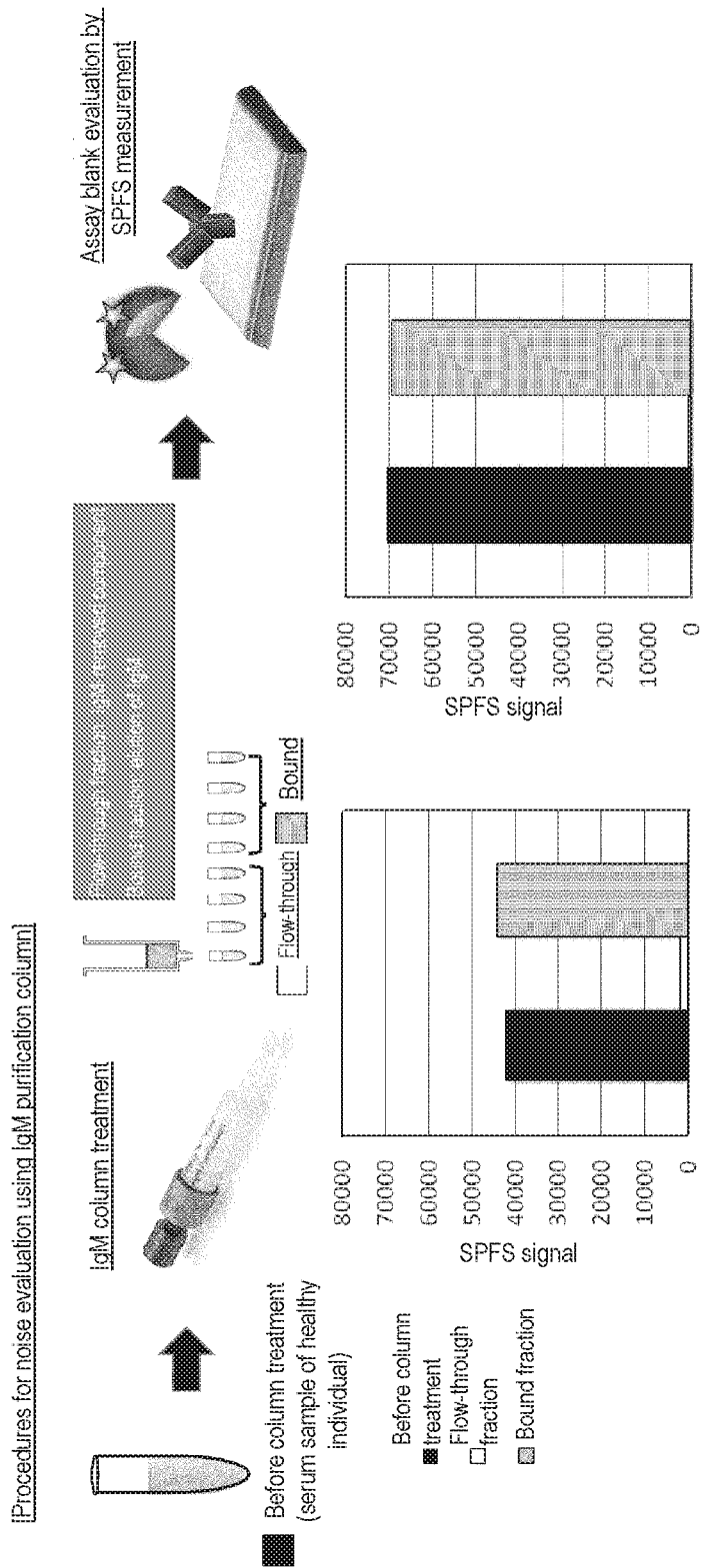

[Fig. 9]
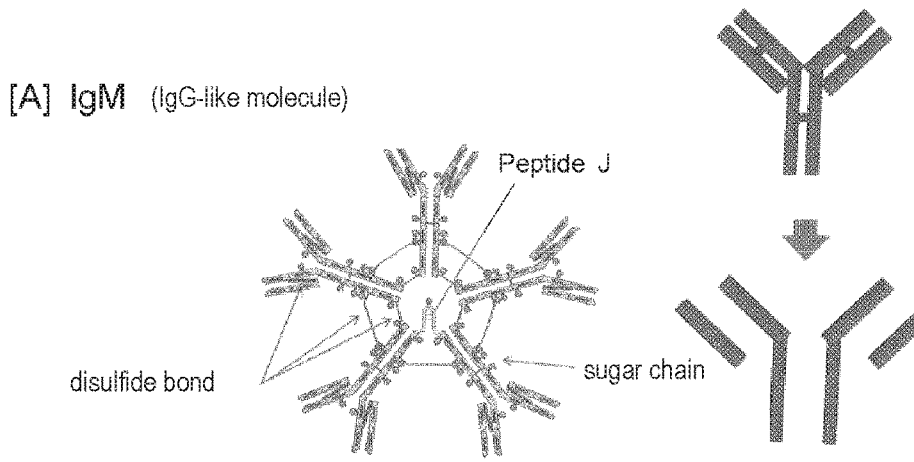
[Fig. 10]
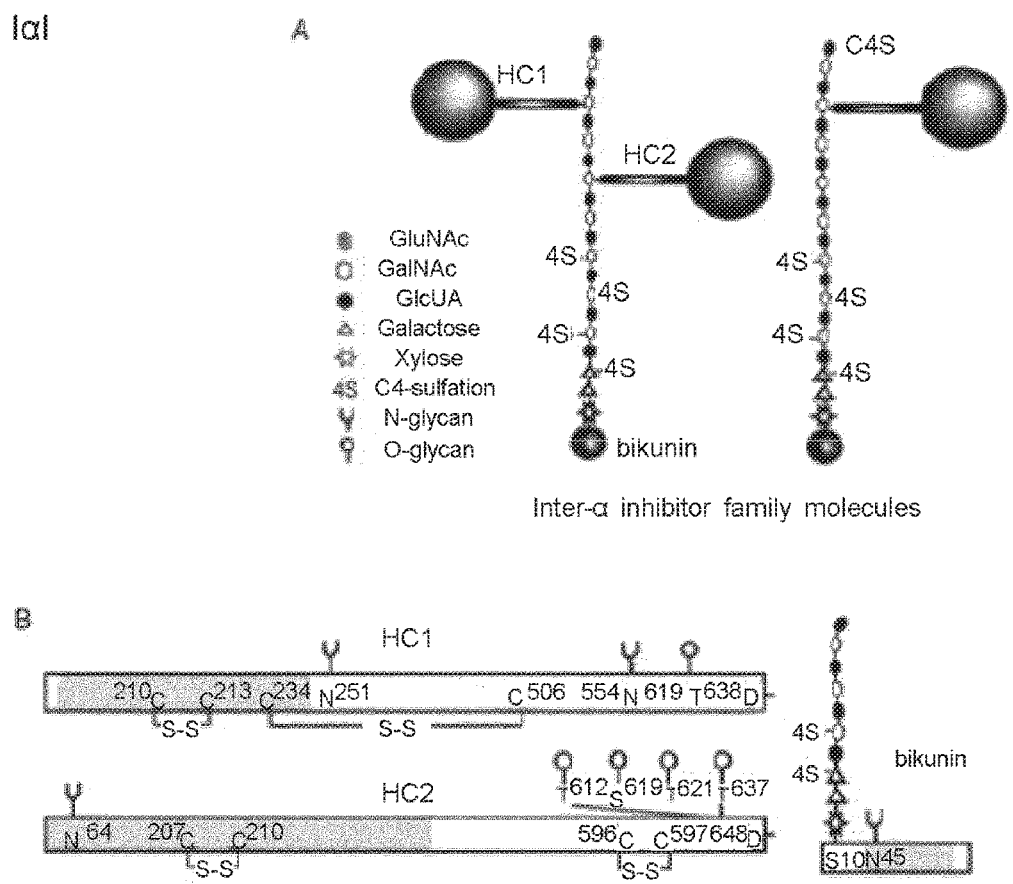

[Fig. 11]
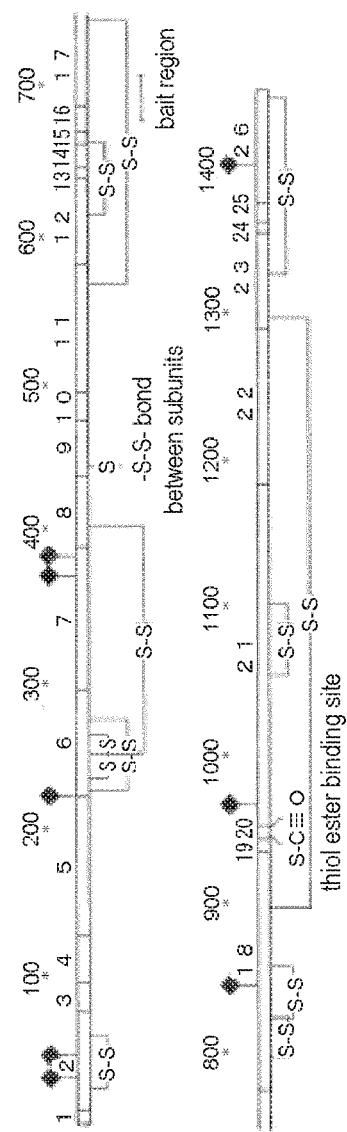

[Fig. 12]
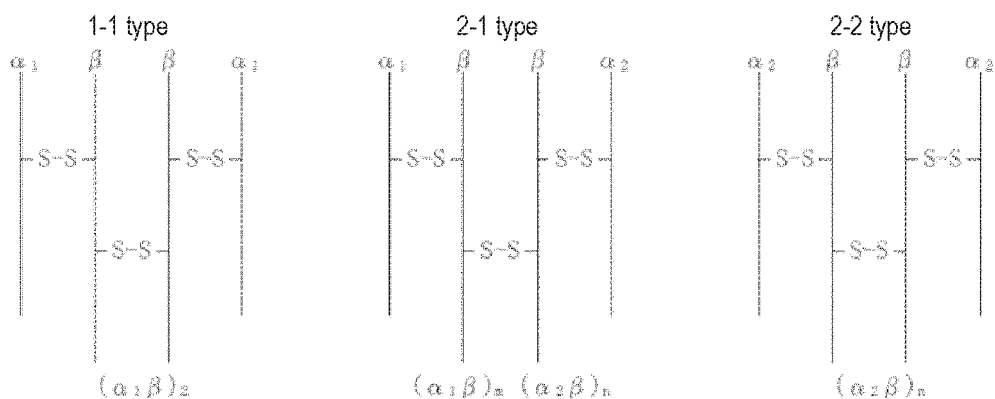

SANDWICH ASSAY USING LABELED LECTIN AND KIT THEREFOR

CROSS REFERENCE TO RELATED APPLICATION

This Application is a 371 of PCT/JP2015/065731 filed on Jun. 1, 2015 which, in turn, claimed the priority of Japanese Patent Application No. JP 2014-127372 filed on Jun. 20, 2014, both applications are incorporated herein by reference.

TECHNICAL FIELD

The present invention relates to a sandwich assay using a labeled lectin and a kit for the same. More particularly, the present invention relates to: a sandwich assay comprising a treatment for inhibiting the binding of a labeled lectin to a contaminant non-specifically adsorbed to a measurement region; and a kit suitable for carrying out a sandwich assay comprising such a treatment.

BACKGROUND ART

In order to allow proteins bearing a principal role in the biological life functions to orderly and properly exhibit their functions in vivo, post-translation modifications including glycosylation play an extremely important role. With regard to the post-translation modifications, the following findings were gradually made in recent years. The majority of the proteins in a living body are modified with sugar chains, and those sugar chains attached to the proteins play important roles in various aspects of biological phenomena, including protein stability, binding with hormones, binding with toxins, viral infection, mycoplasma infection, bacterial infection, protozoan infestation, fertilization, development and differentiation, cancer cell metastasis, apoptosis and the like. Even when proteins have the same amino acid sequence and the same name, such proteins are modified with a wide variety of sugar chains and, depending on the condition of the protein-producing cells, the structures of the sugar chains vary and the proteins thus have different roles in vivo.

The relationships between such changes in sugar chains and diseases have also been gradually elucidated. For example, Patent Document 1 describes as follows with regard to prostate-specific antigens (hereinafter, referred to as "PSAs") which indicate that a subject has a prostate disease. That is, it is described that, as compared to blood samples derived from prostatic hyperplasia patients, those blood samples derived from prostate cancer patients contain a greater amount of a prostate-specific antigen having a specific sugar residue, i.e., an N-acetyl-D-galactosamine β1-4 N-acetylglucosamine (hereinafter, referred to as "LacdiNAc") residue (this prostate-specific antigen is hereinafter referred to as "LacdiNAc-PSA") and/or a fucose-α(1,2)-galactose β1→4 N-acetylglucosamine residue in its sugar chain. This means that the onset of prostate cancer changes the sugar chains of PSAs and this leads to an increase in the amount of PSAs having the above-described specific sugar residue(s), as a result of which a high concentration of PSAs having the specific sugar residue(s) is observed in blood samples of prostate cancer patients. On the other hand, since the onset of prostatic hyperplasia does not cause such a change in the sugar chains, prostatic hyperplasia patients are not observed with a change in the concentration of PSAs having the specific sugar residue(s). On the basis of this, Patent Document 1 discloses a method of distinguishing prostate cancer by fraction measurement of sugar chains, which method is capable of distinguishing a prostate cancer patient from a prostatic hyperplasia patient by measuring, in their blood samples, the concentration of PSAs having the above-described specific sugar residue(s).

In addition, there have been known, for example, such methods of identifying liver cancer by fraction measurement of α-fetoprotein (AFP) sugar chain as disclosed in Patent Document 2 and Non-patent Document 1, as well as such methods of identifying adenocarcinoma by fraction measurement of carcinoembryonic antigen (CEA) sugar chain as disclosed in Non-patent Documents 2 and 3.

For specific detection of a glycoprotein containing a specific sugar residue in its sugar chain, proteins called lectin that are capable of specifically recognizing and binding to such sugar residue are widely utilized. This is because it is very difficult to prepare an antibody whose epitope is a sugar chain, particularly an antibody whose epitope is a specific sugar residue, and such an antibody is thus hardly available. Lectins not only are inexpensive and available in a large amount but also have excellent stability and can thus be stored over a long time.

For example, *Wisteria floribunda* lectin (*Wisteria floribunda* agglutinin: hereinafter, referred to as "WFA") is known to have N-acetylgalactosamine as its primary binding sugar residue. Patent Document 1 discloses a method in which WFA having such a property is bound to a carrier and loaded to a column and a PSA having a LacdiNAc residue in a side chain of an asparagine-linked sugar chain is subsequently fractionated and quantified by ELISA or the like. In addition, Patent Document 3 discloses a method in which a solid-phase anti-PSA antibody and a fluorescently labeled WFA are allowed to form a sandwich complex with a PSA having a LacdiNAc residue in a side chain of its sugar chain and this PSA having the specific sugar residue is then quantified by SPFS (Surface Plasmon-field enhanced Fluorescence Spectroscopy).

Lectins, however, have such drawbacks of having lower binding activity and lower specificity of binding to sugar chains than antibodies. For example, *Wisteria floribunda* lectin (WFA) has N-acetylgalactosamine residue as its primary binding site; however, *Wisteria floribunda* lectin slightly binds with a galactose residue as well. Therefore, when a galactose residue-containing sugar chain exists in a reaction system, *Wisteria floribunda* lectin also binds to this sugar chain and thus cannot be specifically bound only to N-acetylgalactosamine residue-containing sugar chains.

Sandwich assays capable of simply and quantitatively analyzing a specific sugar chain-containing protein (glycoprotein) as a substance to be detected are performed using a lectin having such characteristics in combination with an antibody. An antibody which specifically binds to a protein moiety of a glycoprotein is immobilized on a substrate and used as a solid-phase antibody, and a lectin whose primary binding target is a sugar residue contained in a sugar chain of a glycoprotein is linked with a labeling agent and used as a labeled lectin.

However, although this technique is effective when the substance to be detected, which is a glycoprotein, is purified to a certain extent, since the labeled lectin binds not only to a sugar chain of the substance to be detected but also to sugar chains of contaminants, this technique generates a large background (noise) and shows markedly reduced performance in terms of sensitivity and quantitative capacity in a system that contains a large amount of contaminants, for example, glycoproteins and glycolipids other than the substance to be detected, as in blood, urine and the like that are used as a sample in ordinary disease diagnosis. Therefore, in ordinary diagnosis using blood or the like as a sample, it accompanies a great deal of difficulty to accurately perform a quantitative analysis by a sandwich assay using a lectin and an antibody and, in fact, such a sandwich assay is utilized only in diagnosis where the detection subject is a limited type of glycoprotein that is contained in serum at an extremely high concentration (about several µg/mL).

As methods for reducing the effects (background) of contaminants, there have been examined, for example, a method of using a blocking agent such as bovine serum albumin (BSA) or casein for inhibiting the adsorption of serum contaminants to the surface of a support on which an antibody is immobilized (Patent Document 4); a method of adding an adsorbent, for example, a polymer or a sugar chain complex such as glycosaminoglycan or heparin, for allowing contaminants (non-specific substances), which inhibit antigen-antibody reaction and cause noise, to adsorb thereto and thereby removing the contaminants from the reaction system (Patent Documents 5 and 6); and a method of using a washing liquid having a specific salt strength and a specific formation of surfactant and the like for efficiently removing contaminants adsorbed to a support (Patent Document 4).

However, even with the above-described background-reducing methods, it is an extremely rare case where a drastic effect is attained in a quantitative analysis based on sandwich assay using a lectin and an antibody, and there is also a problem that the search and examination of a blocking agent suitable for the subject of interest require tremendous man-hours.

Meanwhile, the present applicant previously proposed a method of detecting a substance to be detected (analyte) having a detection target sugar chain in a sample using a labeling lectin that binds to plural kinds of sugar chains including the detection target sugar chain and non-detection-target sugar chains, wherein the method comprises: a labeling treatment of bringing the labeling lectin into contact with the substance to be detected prior to the detection step of detecting the substance to be detected bound with the labeling lectin; and a masking treatment of bringing a sugar chain-recognizing molecule for masking, which binds to at least one of the non-detection-target sugar chains, into contact with contaminants having the non-detection-target sugar chains (Patent Document 7). That is, by performing the masking treatment on the non-detection-target sugar chains of contaminants to which the labeling lectin collaterally binds using the sugar chain-recognizing molecule for masking, the labeling lectin is enabled to preferentially bind to the detection target sugar chain contained in the substance to be detected, so that the background noise can be reduced and the detection sensitivity and quantitative performance for the substance to be detected can be improved. As the sugar chain-recognizing molecule for masking, a lectin which mainly recognizes and binds to the non-detection-target sugar chains rather than the detection target sugar chain and is different from the labeling lectin can be used.

However, the method of detecting a substance to be detected according to Patent Document 7 is applicable when a contaminant has a sugar chain containing a sugar residue that is recognized by the same lectin but different from that of the substance to be detected. Further, when such a contaminant is contained in a sample in a large amount, in the invention described in Patent Document 7, since it is required to add a sugar chain-recognizing molecule for masking (a lectin of a type that is different from the labeling lectin) at a high concentration, the reagent cost is increased or else the masking efficiency is reduced. Patent Document 7 discloses neither a means capable of efficiently suppressing the effect of such contaminant having a sugar chain that contains the same sugar residue as the substance to be detected, in a sample in a large amount, nor that the use of such a means can actually markedly improve the measurement sensitivity and quantitative performance for the substance to be detected.

Further, the present applicant has also proposed a method of suppressing non-specific signals in SPFS immunoassay in which a glycoprotein can be a compound to be measured, the method comprising performing at least one of the followings for the suppression of non-specific signals originating from contaminants: a pretreatment of adding an acid or an alkali to a sample; a pretreatment of adding a metal ion to the sample; and a pretreatment of heating the sample (Patent Document 8). By performing these pretreatments to change (modify) the structures of the contaminants, non-specific adsorption of the contaminants to a sensor section can be inhibited. However, in Patent Document 8 as well, there is disclosed no means capable of efficiently suppressing the effects of a contaminant (e.g., glycoprotein) having a sugar chain that contains the same sugar residue as the substance to be detected when such a contaminant is contained in a sample in a large amount.

In terms of these points, sandwich assay using a labeled lectin still has room for improvement.

RELATED ART DOCUMENTS

Patent Documents

[Patent Document 1] WO 2010/090264
[Patent Document 2] JP S61-292062 A
[Patent Document 3] JP 2013-076666 A
[Patent Document 4] JP 2010-127827 A
[Patent Document 5] JP 2009-53195 A
[Patent Document 6] JP 2010-60293 A
[Patent Document 7] JP 2013-253866 A
[Patent Document 8] WO 2014/087802

Non-Patent Documents

[Non-Patent Document 1] Sugar Chains of Human Cord Serum α-Fetoprotein: Characteristics of N-linked Sugar Chains of Glycoproteins Produced in Human Liver and Hepatocellular Carcinomas, K. Yamashita et al., Cancer Res., 53, 1 (1993)
[Non-Patent Document 2] Carbohydrate Structures of Non-specific Cross-reacting Antigen-2, a Glycoprotein Purified from Meconium as an Antigen Cross-reacting with Anticarcinoembryonic Antigen Antibody, K. Yamashita et al., Biol. Chem., 264, 17873 (1989)
[Non-Patent Document 3] Structural Studies of the Carbohydrate Moieties of Carcinoembryonic Antigens, K. Yamashita et al., Cancer Res., 47, 3451 (1987)

SUMMARY OF THE INVENTION

Problems to be Solved by the Invention

An object of the present invention is to provide: a sandwich assay for quantifying a glycoprotein, which is a substance to be detected, in a sample using a labeled lectin, wherein the effect attributed to a contaminant, namely noise on the quantified value of the substance to be detected, is suppressed by introduction of a simple treatment; and a kit suitable for carrying out such a sandwich assay.

Technical Solution

The present inventors have been conducting research and development of a method for diagnosing prostate cancer and prostatic hyperplasia based on the concentration of WFA-binding PSA (i.e. specific PSA having an N-acetylgalactosamine residue-containing sugar chain) contained in a serum sample, which is one of the representative diagnostic methods where sandwich assay using a labeled lectin is applied. When the total PSA concentration was measured in blood samples by ELISA, the total PSA concentration was found to be markedly lower in samples derived from healthy individuals than in those samples derived from patients of prostate cancer and prostatic hyperplasia. In spite of this, when the concentration of the specific PSA having an N-acetylgalactosamine residue-containing sugar chain was measured by SPFS, it was confirmed that the signal value was increased (appearance of abnormally high values) in the samples derived from healthy individuals. This was suggested to cause a reduction in the accuracy of distinguishing prostate cancer patients from healthy individuals, that is, the specificity of prostate cancer diagnosis, in a diagnostic method where SPFS-based sandwich assay is applied.

As a result of further analyses, non-specific binding of several types of glycoproteins contained in serum, such as IgM, to the measurement region was discovered to be a factor of increasing the signal value in samples of healthy individuals. It was found that these glycoproteins also have an N-acetylgalactosamine residue-containing sugar chain in the same manner as the specific PSA and thus bind to WFA, and it was elucidated that these glycoproteins are contained in serum at a constant concentration higher than the specific PSA although the content of each glycoprotein varies among individuals. Therefore, the present inventors speculated that, if the binding of WFA (labeled lectin) to those glycoproteins (contaminants) such as IgM that are non-specifically adsorbed to the measurement region and have the same sugar chain as the specific PSA could be inhibited while maintaining the binding of the labeled lectin to the specific PSA (substance to be detected), large signals (background) acting as noise on the signal for quantifying the specific PSA would be suppressed and the above-described problems can thereby be solved.

In view of this, the present inventors confirmed that, by adding a substance showing an action of cleaving the disulfide bonds of glycoproteins, representative examples of which include reducing agents such as sodium metabisulfite, to serum samples as a treatment for inhibiting the binding of WFA to the same sugar chain as that of the specific PSA that is contained in contaminants such as IgM, the background (noise) can be markedly reduced; and that such a treatment exhibits an unexpectedly excellent effect of improving the S/B ratio in SPFS. Further, the present inventors discovered that such a treatment is applicable not only to those measurement systems using a combination of the specific PSA, IgM and the like along with WFA, but also to other measurement systems in which the sugar chain primarily recognized by a lectin is shared by both the substance to be detected and contaminants; and that the treatment should exert the same actions and effects, thereby completing the present invention.

That is, one aspect of the present invention provides a sandwich assay for quantifying a glycoprotein as a substance to be detected using a labeled lectin and a capturing substance immobilized on a measurement region, wherein the sandwich assay comprises a treatment for inhibiting the binding of the labeled lectin to a sugar chain that is carried by a contaminant non-specifically adsorbed to the measurement region and is the same as that of the substance to be detected.

Further, another aspect of the present invention provides a kit for carrying out a sandwich assay for quantifying a glycoprotein as a substance to be detected using a labeled lectin and a capturing substance immobilized on a measurement region, which kit comprises a substance showing an action of cleaving disulfide bonds for a treatment of a glycoprotein that is a contaminant, and is suitably used for carrying out the sandwich assay of the present invention.

Advantageous Effects of Invention

By the present invention, first of all, it was revealed that samples contain a relatively large amount of a contaminant having the same sugar chain as a substance to be detected and inhibition of the binding of a labeled lectin to such a contaminant non-specifically adsorbed to a measurement region is extremely important in the quantification of the substance to be detected that is performed by highly sensitive sandwich assay such as SPFS. Further, it was also revealed that the binding of a detection lectin to the contaminant can be inhibited by, for example, cleaving disulfide bonds using a reducing agent and thereby allowing a domain that contains the same sugar chain as that of the substance to be detected to dissociate from other domains. Even if other domains of the contaminant remained in the measurement region through non-specific adsorption, since the labeled lectin should no longer bind thereto, an increase in the background (noise) caused by the contaminant can be inhibited (although the labeled lectin may bind to a sugar chain of the dissociated domain, the resulting complex can be relatively easily removed by washing or the like).

By utilizing the sandwich assay of the present invention that exerts such actions and effects, even when a sample containing a relatively large amount of a glycoprotein as a contaminant, such as blood (serum), is used, the substance to be detected such as a tumor marker can be accurately quantified. Particularly, abnormally high measured values are greatly reduced in SPFS-based measurement; therefore, highly reliable diagnosis can be performed with excellent specificity and sensitivity.

BRIEF DESCRIPTION OF DRAWINGS

FIG. 1 is a drawing that schematically shows the state of a measurement region according to one embodiment of the measurement step based on SPFS. FIG. 1[A] shows a case where no cleavage treatment is performed (conventional embodiment), while FIG. 1[B] shows a case where a cleavage treatment is performed (embodiment of the present invention).

FIG. 2 is a drawing that schematically shows the overall constitution of an SPFS measurement apparatus suitable for the use in the present invention. FIG. 2[A] shows an embodiment where a substrate-form member 16a comprises a dielectric member 12, while FIG. 2[B] shows an embodiment where the substrate-form member 16a comprises a transparent planar substrate 13 in place of the dielectric member 12.

FIG. 3 is a partially enlarged view showing the vicinity of the measurement region of the SPFS measurement apparatus shown in FIG. 1. FIG. 3[A] shows an embodiment where the substrate-form member 16a comprises the dielectric member 12, while FIG. 3[B] shows an embodiment where the substrate-form member 16*a* comprises the transparent planar substrate 13 in place of the dielectric member 12.

FIG. 4 provides graphs showing background values (B), signal values (S) and S/B ratios that were measured in Examples and Comparative Examples.

FIG. 5 provides a graph showing the results of measuring the SPFS signal value in Reference Example 1 for a specific PSA contained in the respective samples of prostate cancer patients, prostatic hyperplasia patients and healthy individuals (left); and a graph showing the results of measuring the total PSA value by ELISA for those samples showing a high SPFS signal value among the samples of prostatic hyperplasia patients and healthy individuals (right).

FIG. 6 is a photograph showing the results of Reference Example 1 where samples of healthy individuals were treated using a WFA column and the resulting bound fractions were analyzed by electrophoresis.

FIG. 7 is a graph showing the SPFS signal values measured in Reference Example 1 for sialidase-treated standard reagents of inter-α-trypsin inhibitor (IαI), α2-macroglobulin (α2M), haptoglobin (HP), immunoglobulin M (IgM) and immunoglobulin G (IgG).

FIG. 8 provides graphs showing the SPFS signal values measured in Reference Example 1 for before treatment healthy individual samples as well as flow-through and bound fractions of the healthy individual samples treated using an IgM purification column.

FIG. 9 is a drawing that shows the structure of immunoglobulin M (IgM), which is one of glycoproteins that can be the contaminants in the present invention. It is noted here that immunoglobulin G (IgG) is the same as the IgG-like molecule shown on the right, which is a degradation product of IgM.

FIG. 10 is a drawing that shows the structure of inter-α-trypsin inhibitor (IαI), which is one of glycoproteins that can be the contaminants in the present invention (cited from J. Biol. Chem. 2004, 279:38079-38082).

FIG. 11 is a drawing that shows the structure of α2-macroglobulin (α2M), which is one of glycoproteins that can be the contaminants in the present invention (cited from Protein, nucleic acid and enzyme, Vol. 7 No. 9).

FIG. 12 is a drawing that shows the structure of haptoglobin (HP), which is one of glycoproteins that can be the contaminants in the present invention.

MODE FOR CARRYING OUT THE INVENTION

—Sandwich Assay—

The sandwich assay of the present invention is a sandwich assay for quantifying a glycoprotein as a substance to be detected using a labeled lectin and a capturing substance immobilized on a measurement region, wherein the sandwich assay comprises a treatment for inhibiting the binding of the labeled lectin to a sugar chain that is carried by a contaminant non-specifically adsorbed to the measurement region and is the same as that of the substance to be detected. Although the details of the "measurement region" will be described later, the term "measurement region" refers a region (space) where the intensity of fluorescence emitted therefrom is measured and which comprises an immobilized capturing substance, a support carrying the capturing substance, the surface of a member on which these are arranged, and the like.

The treatment for inhibiting the binding of a labeled lectin to a sugar chain that is carried by a contaminant non-specifically adsorbed to the measurement region and is the same as a sugar chain of the substance to be detected is not particularly restricted and can be modified in accordance with the type of the contaminant (whether it is a glycoprotein or a glycolipid) as well as the substance to be detected, the capturing substance, the labeled lectin, the measurement system and the like. In the present specification, the present invention will be described primarily based on an embodiment where the contaminant is a "glycoprotein" having the same sugar chain as the substance to be detected; however, even in those cases where the contaminant is a "non-glycoprotein substance" (e.g., a glycolipid) having the same sugar chain as the substance to be detected, the present invention can be carried out by applying the following descriptions such that the expected actions and effects are exerted.

<S—S Bond-Cleaving Agent>

In a typical embodiment of the present invention, the contaminant non-specifically adsorbed to the measurement region is a glycoprotein that has the same sugar chain as the substance to be detected. In this case, the treatment for inhibiting the binding of the labeled lectin to the sugar chain is preferably a treatment in which a substance showing an action of cleaving disulfide bonds (hereinafter, referred to as "S—S bond-cleaving agent") is brought into contact with a glycoprotein that is a contaminant and its domain containing the same sugar chain as that of the substance to be detected is thereby dissociated.

The substance showing an action of cleaving disulfide bonds of the contaminant (S—S bond-cleaving agent) is not particularly restricted; however, it is preferably, for example, a reducing agent, that is, a compound which shows an action of reducing a cross-linked structure (—S—S—) into two sulfhydryl groups (—SH and HS—; thiol groups).

The reducing agent is not particularly restricted and can be selected from a variety of reducing agents that are used for cleaving disulfide bonds of proteins. Examples of such a reducing agent include salts of lower oxyacids such as sulfurous acid, hyposulfurous acid, phosphorous acid and hypophosphorous acid; alkali hydroxides; and thiol salts functioning as nucleophiles. Specifically, for example, sodium metabisulfite, thioglycerol, sodium toluenethiosulfinate, 2-mercaptoethanol, dithiothreitol (DTT), 2-mercaptoethylamine hydrochloride, 2-aminoethylisothiouronium bromide hydrobromide and tris(2-carboxyethyl)phosphine can be used and, thereamong, sodium metabisulfite is particularly preferred.

As the S—S bond-cleaving agent, in addition to the above-described compounds, disulfide reductase can also be used.

<Substance to be Detected>

In the present invention, the substance to be detected is a glycoprotein comprising: a sugar chain that contains a specific sugar residue which an appropriate lectin recognizes and binds to; and a site (particularly a protein moiety) which an appropriate antibody recognizes and binds to.

A typical example of the glycoprotein used as the substance to be detected is a marker molecule that is contained in a sample of interest and used for pathological diagnosis. The substance to be detected is preferably, for example, a tumor antigen/tumor marker such as PSA, AFP or CEA, and the substance to be detected can also be a signal transducer or a glycoprotein such as a hormone.

In a preferred embodiment of the present invention, a PSA having an N-acetyl-D-galactosamine β1-4 N-acetylglucosamine (hereinafter, abbreviated as "LacdiNAc") residue-containing sugar chain (such a PSA is hereinafter abbreviated as "LacdiNAc-PSA") is the substance to be detected.

The substance to be detected is preferably a glycoprotein which contains the same sugar chain as that of the contaminant and a binding site for the capturing substance within the same domain, in other words, a glycoprotein in which a domain containing the same sugar chain as that of the contaminant and a domain containing the binding site for the capturing substance are not separated by an S—S bond-cleaving agent. As long as the substance to be detected is such a glycoprotein, even if an S—S bond-cleaving agent for the contaminant comes into contact with the substance to be detected and the domains of the substance to be detected are partially dissociated, both the capturing substance and the labeled lectin are still capable of binding to the domain which contains the same sugar chain as that of the contaminant and a binding site for the capturing substance and a sandwich complex can thereby be formed in the measurement region; therefore, a treatment targeting the contaminant can be prevented from affecting the quantification of the substance to be detected.

<Contaminant>

In the present invention, the contaminant, whose effects on the quantification of the substance to be detected are to be suppressed, is a substance having the same sugar chain as that of the substance to be detected. Specifically, glycoproteins, glycolipids and other sugar chain-containing biologically relevant substances (e.g., low-molecular-weight substances) other than the substance to be detected that exist in a sample along with the substance to be detected can be such a contaminant.

In a typical embodiment of the present invention, a glycoprotein such as immunoglobulin M (IgM), inter-α-trypsin inhibitor (IαI), α2-macroglobulin (α2M), haptoglobin (HP) or immunoglobulin G (IgG) is the main contaminant to be suppressed. The structures of these glycoproteins are shown in FIGS. 9 to 12. All of these glycoproteins exist in serum at a relatively high concentration (about several mg/mL) and have a large effect as noise against the measured signal even when their rate of non-specific adsorption to the measurement region is minimal. Further, these five types of glycoproteins all have a plurality of sugar chains that constitute different sugar residues, with at least one of the sugar chains being an N-acetyl-D-galactosamine β1-4 N-acetylglucosamine residue-containing sugar chain. However, the constitutional ratios of these five types of glycoproteins in serum and the ratio of the sugar chains (sugar residues) contained in each glycoprotein vary among samples, namely depending on whether or not the subject has a specific disease and other individual differences, and this causes noise (background) that has been conventionally difficult to suppress uniformly.

An IgM is a molecule that exists in blood usually at a concentration of 0.3 to 2.5 mg/mL and has 50 or more N-linked sugar chains in the molecule. An IgM is a multimer (pentamer or hexamer) having a structure in which five or six IgG-like molecules are linked together via disulfide bonds.

An IαI is a molecule that exists in blood usually at a concentration of about 0.5 mg/mL, and has four N-linked sugar chains and four O-linked sugar chains in the molecule. In an IαI, three domains of H1 heavy chain, H2 heavy chain and bikunin are linked by one chondroitin sulfate chain, and each IαI has four disulfide bonds in the molecule.

A α2M is a macromolecule that exists in serum usually at a concentration of 1 to 2.5 mg/mL and is formed by association of 4 subunits each of which has a molecular weight of 160,800 and contains eight N-linked sugar chains. The subunits of α2M are bound with each other via disulfide bonds, and a number of disulfide bonds also exist within each subunit.

An HP is a molecule that exists in blood usually at a concentration of 0.1 to 1.7 mg/mL and has a structure in which two α-chains and two β-chains having four N-linked sugar chains are linked together via disulfide bonds. There are two types of α-chains, $α_1$ and $α_2$, with a single type of β-chain, and HP has three genotypes depending on the combination thereof: 1-1 type, 2-1 type and 2-2 type.

An IgG is a molecule that exists in blood usually at a high concentration of 8.7 to 18.1 mg/mL and has at least two N-linked sugar chains in the molecule. An IgG has three disulfide bonds in the molecule, and two H-chains [heavy chains] and two L-chains [light chains] exist in a bound state.

In the above-described manner, the 5 types of glycoproteins all contain S—S bonds and can be fragmented or deformed by cleaving the S—S bonds; therefore, a treatment with a disulfide bond cleaving agent is an effective means for inhibiting non-specific adsorption. For example, when an S—S bond-cleaving agent is applied to IgM, the disulfide bonds linking the IgG-like molecules are cleaved and IgM is degraded into individual IgG-like molecules. Further, depending on the strength of the effect of the S—S bond-cleaving agent, the three disulfide bonds existing in each IgG-like molecule are also cleaved and the IgG-like molecules are eventually degraded into two light chains and two-heavy chains. The other glycoproteins can also be degraded in the same manner into the subunits or domains that are described above for each glycoprotein.

Such degradation or deformation of the contaminant by cleavage of S—S bonds not only causes the contaminant to lose its ability of non-specifically adsorbing to the measurement region but also, even if a partial degradation product of the contaminant non-specifically adsorbed to the measurement region, enables to inhibit the generation of noise as long as the moiety modified with a sugar chain containing a specific sugar residue capable of reacting with a labeled lectin is dissociated from the partial degradation product.

Since a prominent effect is actually observed when an S—S bond-cleaving agent is allowed to act on IgM, it is thought that IgM non-specifically adsorbs to the measurement region probably at an antigen recognition site (Fab region of IgG-like molecule); and that (a part or the entirety of) the moiety modified with a sugar chain containing a specific sugar residue, which a lectin recognizes and binds to, exists in a region that is apart from the antigen recognition site by at least one disulfide bond. A similar effect is also observed when an S—S bond-cleaving agent is allowed to act on the above-exemplified other substances; therefore, the moiety non-specifically adsorbing to the measurement region and (a part or the entirety of) the moiety modified with a sugar chain containing a specific sugar residue which a lectin recognizes and binds to are believed to exist apart from each other by at least one disulfide bond.

In the below-described Reference Examples, a focus is given to IgM; however, the interpretation of the actions and effects of the present invention should not be restricted to those cases where IgM is the contaminant. It has been shown that contaminants other than IgM, such as IαI, α2M, HP and IgG, also causes noise on SPFS signals although the extent thereof varies and, therefore, in order to perform an analysis with the highest possible sensitivity and specificity, it is also effective to suppress the noise of such contaminants. Furthermore, as described above, the constitutional ratio of these contaminants and the ratio of a sugar chain contained in a contaminant vary among samples, and it is highly likely that, for those samples that are different from the ones used in the below-described Reference Examples, a contaminant other than IgM, such as IαI, α2M, HP or IgG, acts as a major factor of causing noise. Therefore, it should be understood that the present invention can universally exert its actions and effects against IgM, IαI, α2M, HP and IgG as well as other contaminants which have the same sugar chain as the substance to be detected and are contained in a relatively large amount in samples such as serum and to which the same labeled lectin may potentially bind.

<Sample>

In the present invention, a sample that potentially contains the substance to be detected and a contaminant is used. The sample that potentially contains the substance to be detected and a contaminant may be a sample actually containing them or a sample that does not actually contain them. Specifically, the sample may be, for example, one derived from a patient of a specific disease that is highly likely to contain the substance to be detected (and contaminant) or one derived from a healthy individual that is unlikely to contain the substance to be detected (and contaminant). Further, the subject from which the sample is collected is typically a human; however, it may also be a non-human mammal, examples of which include human disease model animals such as mice, rats, guinea pigs, rabbits, goats, cats, dogs, pigs and monkeys.

Examples of the sample include biological samples and samples derived from living bodies, such as blood, urine, spinal fluid, saliva, cells, tissues, organs, and preparations thereof (e.g., biopsy specimens). For example, blood and urine are preferred as the sample used in the sandwich assay of the present invention since they potentially contain not only a glycoprotein that can be utilized as a diagnostic marker but also a relatively large amount of other glycoproteins as contaminants.

Liquid samples such as blood, serum, plasma, urine, spinal fluid and saliva may be diluted with an appropriate buffer before use. Further, solid samples such as cells, tissues and organs can be homogenized with an appropriate buffer to about 2 to 10 times by volume and the resulting suspension or supernatant thereof can be used as is or after further dilution.

In a preferred embodiment of the present invention, blood is used as the sample. This blood may be whole blood, or serum or plasma prepared from whole blood. For example, when it is aimed at performing the measurement quickly, whole blood may be used as the sample or, when it is aimed at performing accurate quantification, the blood cell components may be removed from whole blood by centrifugation or the like and the thus prepared serum or plasma may be used as the sample. Further, at the time of blood collection, an anticoagulant is usually added to the collected whole blood, and the whole blood, serum and plasma are diluted with a diluent (e.g., buffer) to an appropriate concentration upon being subjected to a measurement by SPFS or the like, followed by a further addition of a necessary reagent (s) and the like. In the present specification, such whole blood, serum or plasma that is used as a sample to which an anticoagulant, a diluent, other reagent (s) and the like may be added as required is referred to as "blood sample".

<Labeled Lectin>

In the present invention, a lectin which is capable of recognizing and binding to a specific sugar residue contained in a sugar chain of the substance to be detected is labeled and used for sandwich assay. It is noted here that substances called "agglutinin" are also included in lectins; however, they are also uniformly referred to as "lectins".

The lectin used in the present invention is appropriately one which primarily recognizes and binds to a specific sugar residue contained in a sugar chain of the substance to be detected. In other words, since lectins generally show different binding strengths to plural kinds of sugar residues, it is appropriate to use a lectin that exhibits the strongest binding strength to a sugar residue of the substance to be detected.

There are diverse types of lectins that originate from a variety of animals, plants, fungi, bacteria and viruses. Such lectins can be obtained from these materials through separation, extraction and purification, and they are also available as commercial products. Specific examples of known lectins include: ACA (*Amaranthus cauciatus* lectin), BPL (*Bauhinia purpurea* lectin), ConA (*Canavalia ensiformis* lectin), DBA (Horsegram lectin), DSA (*Datura stramonium* lectin), ECA (*Erythrina cristagalli* lectin), EEL (Spindle Tree lectin), GNA (*Galanthus nivalis* lectin), GSL I (*Griffonia simplicifolia* lectin I), GSL II (*Griffonia simplicifolia* lectin II), HHL (*Hippeastrum* hybrid lectin), jacalin (jackfruit lectin), LBA (Lima bean lectin), LCA (*Lens culinaris* lectin), LEL (*Lycopersicon esculentum* lectin), LTL (*Lotus tetragonolobus* lectin), MPA (*Maclura pomifera* lectin), NPA (*Narcissus pseudonarcissus* lectin), PHA-E (*Phaseolus Vulgaris* lectin-E), PHA-L (*Phaseolus Vulgaris* lectin-L), PNA (peanut lectin), PSA (*Pisum sativum* lectin), PTL-I (*Psophocarpus tetragonolobus* lectin-I), PTL-II (*Psophocarpus tetragonolobus* lectin-II), PWM (pokeweed lectin), RCA120 (*Ricinus communis* lectin), SBA (soybean lectin), SJA (*Sophora japonica* lectin), SNA (*Sambucus nigra* lectin), SSA (*Sambucus sieboldiana* lectin), STL (*Solanum tuberosum* lectin), TJA-I (*Trichosanthes japonica* lectin-I), TJA-II (*Trichosanthes japonica* lectin-II), UDA (common stinging nettle lectin), UEA I (*Ulex europaeus* lectin), VFA (*Vicia faba* lectin), VVL (*Vicia villosa* lectin or *Vicia sativa* lectin), WFA (*Wisteria floribunda* lectin), WGA (wheat germ lectin), AAL (*Aleuria aurantia* lectin), and AOL (*Aspergillus oryzae* lectin). From these lectins, one that is appropriate can be selected and used in the present invention as described above.

In a preferred embodiment of the present invention, WFA which primarily binds to a LacdiNAc residue is used for the preparation of a labeled lectin. Since the LacdiNAc residue is contained not only in the above-described specific PSA (LacdiNAc-PSA) but also in IgM which is a contaminant having a large effect on the quantification of the specific PSA, WFA is strongly reactive with both LacdiNAc-PSA and IgM. Further, SBA (soybean lectin), VVL (*Vicia sativa* lectin) and TJA-II (*Trichosanthes japonica* lectin) also show strong binding to the LacdiNAc residue and can thus be preferably used in the present invention in the same manner as WFA.

The labeled lectin can be prepared by binding a desired label to a lectin in accordance with a known and commonly used method, and a variety of commercially available kits (labeling kits) can be used for the preparation.

As the label, one which conforms to the measurement system of the sandwich assay can be used. For example, a fluorescent dye is generally used in SPFS while an enzyme is generally used in ELISA; however, other known labels, such as phosphors other than fluorescent dyes (e.g., fluorescent proteins and fluorescent fine particles), chemiluminescent substances and radioactive substances can also be used.

Examples of a fluorescent dye that can be used in SPFS and the like include organic fluorescent dyes such as fluorescent dyes of the fluorescein family (manufactured by Integrated DNA Technologies, Inc.), fluorescent dyes of the polyhalofluorescein family (manufactured by Applied Biosystems Japan, Ltd.), fluorescent dyes of the hexachlorofluorescein family (manufactured by Applied Biosystems Japan, Ltd.), fluorescent dyes of the coumarin family (manufactured by Invitrogen Corp.), fluorescent dyes of the rhodamine family (manufactured by GE Healthcare Bio-Sciences Corp.), fluorescent dyes of the cyanine family, fluorescent dyes of the indocarbocyanine family, fluorescent dyes of the oxazine family, fluorescent dyes of the thiazine family, fluorescent dyes of the squaraine family, fluorescent dyes of the chelated lanthanide family, fluorescent dyes of the BODIPY (registered trademark) family (manufactured by Invitrogen Corp.), fluorescent dyes of the naphthalene sulfonate family, fluorescent dyes of the pyrene family, fluorescent dyes of the triphenylmethane family, and Alexa Fluor (registered trademark) dye series (manufactured by Invitrogen Corp.); and rare earth (e.g., Eu, Tb) complex-based fluorescent dyes (such as ATBTA-Eu$^{3+}$).

Representative examples of an enzyme that can be used in ELISA and the like include horseradish-derived peroxidase (HRP) and alkaline phosphatase (ALP), and these enzymes can each be used in combination with a corresponding and appropriate substrate.

<Capturing Substance>

In the present invention, a substance which specifically binds to a glycoprotein that is the substance to be detected is immobilized on the measurement region. This enables to capture the substance to be detected in the measurement region and to thereby form a complex of [capturing substance-substance to be measured-labeled lectin] (sandwich complex).

The capturing substance is not particularly restricted as long as it is an appropriate substance that corresponds to the substance to be detected and, for example, an antibody, an aptamer or a synthetic peptide can be used. In a typical embodiment of the present invention, an antibody which specifically recognizes and binds to a glycoprotein that is the substance to be detected, particularly a protein moiety thereof, without interfering with the sugar chain recognition by a lectin, is used as the capturing substance.

The antibody against the substance to be detected is not particularly restricted as long as it can be prepared by a commonly used method when the substance to be detected is regarded as an antigen; however, from the standpoint of the measurement stability (reproducibility), a monoclonal antibody is more preferred than a polyclonal antibody. Further, in order not to interfere with the binding of labeled lectin to a specific sugar residue in a sugar chain, the antibody is preferably one whose epitope is not a sugar chain but a protein moiety of a glycoprotein.

For example, for those cases where a tumor antigen/tumor marker is the substance to be detected, a variety of anti-tumor antigen/tumor marker monoclonal antibodies have been developed and are available as commercial products. Examples of monoclonal antibodies against PSA (anti-PSA monoclonal antibodies) that are known as markers of prostate cancer and the like include PS2, PS3, PS4, PS5, PS6, PS15, 2H9, 3B4, 5A6, 5G6, 8G4, 9A8, 9G2, PS1, 8A6, 2H9, 1H12 and No. 79 and the like.

It is noted here that the term "antibody" used in the present specification has a broad meaning that includes not only complete antibodies but also antibody fragments and derivatives. Those matters described with the term "antibody" can be carried out using an antibody fragment or derivative, such as Fab, Fab'$_2$, CDR, a humanized antibody, a polyfunctional antibody or a single-chain antibody (ScFv), in the same manner as in the case where each matter is carried out using a complete antibody.

For immobilization of an antibody and other capturing substance, a "support" that carries them may be used as required. The support is not particularly restricted as long as it conforms to the measurement system, and examples thereof include insoluble polysaccharides such as agarose, cellulose and dextran; synthetic resins such as silicon resins, polystyrene resins, polyacrylamide resins, nylon resins and polycarbonate resins; and insoluble supports made of glass or the like.

Further, the support may be of a desired form that conforms to the measurement system, such as beads (mainly spherical) or a plate (mainly planar). As beads, for example, magnetic beads or resin beads and the like that are filled in a column or the like can be used. In the case of a plate-form support, for example, a multi-well plate (e.g., a 96 multi-well plate) or a biosensor chip can be used.

For immobilization of a capturing substance, a known immobilization mode such as chemical bonding or physical adsorption can be employed. For example, in order to immobilize an antibody on the surface of a sensor chip used in SPFS, a modifying group reactive with a functional group (e.g., an amino group or a carboxyl group) of the antibody is introduced to the surface of a metal thin film or the like of the sensor chip using a silane-coupling agent, a linker, a support or the like and the modifying group and the functional group of the antibody are allowed to react with each other in the presence of a prescribed reaction reagent as required, whereby the antibody can be immobilized on the support via a covalent bond. Particularly, an antibody can be immobilized on the sensor chip surface at a high density by first forming a layer made of a hydrophilic polymer such as a polysaccharide (e.g., carboxymethyldextran (CMD)) on the metal thin film surface as a support and then allowing the antibody to bind with the reactive groups of the hydrophilic polymer, such as a large number of carboxyl groups that are contained in carboxymethyldextran and have been converted into active esters using a prescribed reagent, and this process is preferred from the standpoint of, for example, improving the reaction efficiency.

<Steps Included in Sandwich Assay>

In a sandwich assay, when a measurement region is arranged on the surface of a measuring member and a complex of [capturing substance-substance to be detected-labeled lectin] (sandwich complex) is formed thereon, the intensity of a signal emitted from the labeled lectin existing in the measurement region is measured and the content (concentration) of the substance to be detected in a sample is quantified based on the thus measured value. Generally, such a sandwich assay is broadly divided into "the pre-measurement step" where various treatments are performed for forming a sandwich complex prior to the signal measurement; and "the measurement step" where, after the formation of the sandwich complex, various treatments are performed for measuring the signal.

[Pre-Measurement Step]

When the contaminant is a "glycoprotein" having the same sugar chain as the substance to be detected, it is preferred that the pre-measurement step comprise a process of allowing a substance showing an action of cleaving disulfide bonds (S—S bond-cleaving agent) to act on the contaminant. In this case, the pre-measurement step generally comprises the following three treatments (A) to (C):

(A) a treatment of bringing a labeled lectin into contact with a substance to be detected (labeling treatment);

(B) a treatment of bringing an S—S bond-cleaving agent into contact with a contaminant (cleavage treatment); and (C) a treatment of bringing the substance to be detected (and the contaminant) into contact with a capturing substance (capturing treatment).

The labeling treatment (A), cleavage treatment (B) and capturing treatment (C) can be performed in a variety of orders depending on the embodiment of the pre-measurement step. In any embodiment, even if there is a contaminant non-specifically adsorbed to the measurement region, its domain having the same sugar chain as that of the substance to be detected is removed from the contaminant at the stage where a complex of [capturing substance-substance to be detected-labeled lectin] is formed. Specific examples of the order of performing the labeling treatment, cleavage treatment and capturing treatment are shown below. It is noted here that the symbol "+" represents that the treatments shown on each side of the symbol are performed simultaneously, while the symbol "→" means that the treatment shown on the left of the symbol is performed before the treatment shown on the right. For instance, "(labeling treatment+cleavage treatment)→capturing treatment" indicates that the labeling treatment and the cleavage treatment are performed simultaneously and the capturing treatment is performed thereafter.

(Order of Treatments in Pre-Measurement Step)

(1) (labeling treatment+cleavage treatment)→capturing treatment (2) labeling treatment→cleavage treatment→capturing treatment (3) cleavage treatment→labeling treatment→capturing treatment (4) cleavage treatment→capturing treatment→labeling treatment (5) labeling treatment→capturing treatment→cleavage treatment (6) capturing treatment→(labeling treatment+cleavage treatment)

(7) capturing treatment→labeling treatment→cleavage treatment (8) capturing treatment→cleavage treatment→labeling treatment The order of the cleavage treatment in the pre-measurement step can be largely classified into two groups: group (I) where the cleavage treatment is performed before the capturing treatment, which corresponds to the orders (1) to (4); and group (II) where the cleavage treatment is performed after the capturing treatment, which corresponds to the orders (5) to (8).

In the case of the group (I), an S—S bond-cleaving agent is brought into contact with a contaminant (glycoprotein) before the contaminant is brought into contact with a capturing substance. For example, the S—S bond-cleaving agent (which may be in the form of a solution) is added and mixed to a sample and the like containing the contaminant along with the substance to be detected or other sample before bringing the sample or the like into contact with the measurement region on which the capturing substance is immobilized. By going through this cleavage treatment, the possibility of a domain having a prescribed sugar chain in the contaminant to non-specifically adsorb to the measurement region in the capturing treatment can be reduced.

In the case of performing the order (1), the S—S bond-cleaving agent and the labeled lectin can be simultaneously added to the sample or the like and then the sample or the like can be brought into contact with the capturing substance. Meanwhile, in the case of performing the order (2), the labeled lectin is added to the sample or the like and then the S—S bond-cleaving agent is further added and, in the case of performing the order (3), the S—S bond-cleaving agent is added to the sample or the like and then the labeled lectin is further added, in either of which cases the sample or the like can be brought into contact with the capturing substance thereafter. Further, in the case of the order (4), after adding the S—S bond-cleaving agent to the sample or the like and subsequently bringing the sample or the like into contact with the capturing substance, a solution of the labeled lectin can further be brought into contact with the capturing substance.

In the case of the group (II), an S—S bond-cleaving agent is brought into contact with a contaminant (glycoprotein) after the contaminant is brought into contact with a capturing substance. In this case, it is possible that the contaminant, which is in a state where its domain having a prescribed sugar chain is not cleaved, adsorbs non-specifically to the measurement region; therefore, by performing the cleavage treatment on the non-specifically adsorbed contaminant, the domain having a prescribed sugar chain is dissociated from the support.

In the case of performing the order (5), after adding the labeled lectin to the sample or the like and subsequently bringing the sample or the like into contact with the capturing substance, a solution of the S—S bond-cleaving agent can be further brought into contact with the capturing substance. Meanwhile, in the case of performing the order (6), after bringing the sample or the like into contact with the capturing substance, a solution in which both the S—S bond-cleaving agent and the labeled antibody are dissolved can be brought into contact with the resultant. In the case of performing the order (7), the sample or the like is brought into contact with the capturing substance and then a solution of the labeled antibody is brought into contact therewith, after which a solution of the S—S bond-cleaving agent can be further brought into contact with the resultant. Further, in the case of performing the order (8), the sample or the like is brought into contact with the capturing substance and then a solution of the S—S bond-cleaving agent is brought into contact therewith, after which a solution of the labeled antibody can be further brought into contact with the resultant.

However, in the group (II) where the cleavage treatment is performed after the capturing treatment, that is, in the orders (5) to (8), the S—S bond-cleaving agent also acts on an antibody immobilized on the support and this potentially affects the ability of capturing the substance to be detected. In the present invention, therefore, as in the case of the group (I) where at least the cleavage treatment is performed before the capturing treatment, that is, as in the orders (1) to (4), it is preferred that the S—S bond-cleaving agent (e.g., reducing agent) be brought into contact with the contaminant (glycoprotein) before the contaminant is brought into contact with the capturing substance.

The conditions, such as the types and concentrations of the labeled lectin and S—S bond-cleaving agent that are used for the above-described labeling treatment and cleavage treatment and the processing time thereof, can be determined taking into consideration the reactivity between the substance to be detected and the labeled lectin as well as the reactivity between the S—S bond-cleaving agent and the glycoprotein as the contaminant and in accordance with the embodiment of the measurement system utilized for the sandwich assay such that the expected actions and effects are exerted, and those of ordinary skill in the art should be able to appropriately set such conditions without having to bear undue trial and error.

As for the S—S bond-cleaving agent, for example, when a reducing agent is added to the sample or the like in any of the above-described orders (1) to (4), generally, the reducing agent can be added to the sample such as serum at a final concentration of 1 mM to 1M and allowed to react for 1 minute to 60 minutes. The larger the added amount of the S—S bond-cleaving agent, the more quickly are the S—S bonds of the contaminant cleaved and the more likely is the contaminant broken into low-molecular-weight fragments.

[Measurement Step]

The measurement step is the step of measuring the intensity of a signal emitted from the labeled lectin, and the embodiment thereof conforms to a measurement system using a sandwich assay.

For example, in an SPFS-based measurement system, a lectin linked with a fluorescent dye is generally used as a labeled lectin; therefore, in the measurement step, an excitation light corresponding to the fluorescent dye is irradiated and the intensity of generated fluorescence is measured using a detector.

Further, in an ELISA-based measurement system, a lectin linked with an enzyme is used as a labeled lectin; therefore, in the measurement step, a substrate corresponding to the enzyme is added and the intensity of generated fluorescence is measured using a detector.

(Embodiment According to SPFS)

The sandwich assay of the present invention is preferably carried out in accordance with an SPFS (surface plasmon-field enhanced fluorescence spectroscopy) measurement system. As described below, SPFS is capable of measuring the intensity of fluorescence emitted from a labeled lectin with high sensitivity; however, the measured value of fluorescence intensity (signal: S) is that much more likely to include not only the signal that originated from a labeled lectin bound to the substance to be detected and should be measured, but also the background (B) that originated from a labeled lectin and the like bound to a contaminant and thus should not be measured. The cleavage treatment performed in the above-described pre-measurement step markedly reduces such noise and thereby improves the S/B ratio used as an index of the quantitative value of the substance to be detected, enabling more accurate quantification of the substance to be detected.

SPFS is a method which utilizes a phenomenon that, when an excitation light is irradiated to a metal thin film formed on a dielectric member at an angle that causes attenuated total reflection (ATR), an evanescent wave transmitting through the metal thin film is enhanced by several ten times to several hundred times due to resonance with surface plasmon, so as to efficiently excite a fluorescent substance labeling a substance to be measured that is captured in the vicinity of the metal thin film. By measuring the intensity of the fluorescence emitted from the fluorescent substance, the substance to be detected can be quantified based on the measured value. As required, this measured value is compared with a value obtained by measuring the fluorescence intensity using a standard sample having a known concentration, and the measured value can thereby be converted into the concentration of the substance to be detected that is contained in a sample. Such SPFS is extremely sensitive as compared to common fluorescent labeling methods and the like; therefore, it is capable of determining the concentration of a substance to be detected even when the substance is contained in a sample at an extremely low concentration.

First, the state of the measurement region when the measurement step is carried out based on SPFS will be described referring to FIG. 1. In both FIGS. 1A and 1B, a metal thin film 14 is formed on a dielectric member 12, and a support 54, which is composed of a hydrophilic polymer such as carboxymethyldextran and carries a capturing substance 50, is arranged thereon as a reaction layer, constituting a measurement region 38.

FIG. 1A shows the state of a case where the cleavage treatment is not performed (conventional embodiment). A substance to be detected 60 binds to the capturing substance 50 carried on the support 54 and a labeled lectin 52 having a fluorescent substance 52a binds to a sugar chain 60a of the substance to be detected 60, thereby forming a complex. Meanwhile, a contaminant 62, which has a sugar chain 62a containing the same sugar residue as that of the sugar chain 60a of the substance to be detected 60, adsorbs non-specifically to the support 54 and the capturing substance 50, and the labeled lectin 52 also binds to this sugar chain 62a. Therefore, the fluorescence emitted from the measurement region 38 includes fluorescence (signal) that indicates the presence of the substance to be detected 60 as well as fluorescence (background) originated from the non-specifically adsorbed contaminant.

In contrast, FIG. 1B shows the state of a case where the cleavage treatment is performed (embodiment of the present invention). As in the case shown in FIG. 1A, the substance to be detected 60 binds to the capturing substance 50 carried on the support 54 and the labeled lectin 52 having the fluorescent substance 52a binds to the sugar chain 60a of the substance to be detected 60, thereby forming a complex. However, the contaminant 62 is fragmented into domains 62b by the cleavage treatment, and non-specific adsorption of the domains 62b having the sugar chain 62a to the support 54 and the capturing substance 50 is thereby inhibited. Therefore, the fluorescence emitted from the measurement region 38 is mainly the fluorescence (signal) that indicates the presence of the substance to be detected 60, and the fluorescence (background) originated from the non-specifically adsorbed contaminant can be eliminated almost entirely.

The fundamental constitutions for performing SPFS, namely embodiments of a measuring member (e.g., sensor chip), a measurement apparatus, a system, measurement procedures and the like are known (see, for example, JP 2013-253866 A: Patent Document 7 and WO2014/087802: Patent Document 8), and they can be applied to appropriately carry out the present invention. The general outlines of an SPFS measurement apparatus and a measuring member (as well as a system integrating these components) will now be described referring to FIGS. 2 and 3.

The measuring member for SPFS is a member generally referred to as "sensor chip 16" and has a constitution in which a substrate-form member 16a, on which a measurement region for forming a sandwich-type immunocomplex and performing fluorescence measurement by SPFS is formed, is laminated with a flow channel member 16b for constituting a flow channel 36, which is capable of introducing to and retaining on the measurement region a variety of solutions (e.g., a sample containing the substance to be detected or other sample, a labeled lectin solution and other necessary reagents) that are used for the formation of the sandwich complex and the like. The sensor chip 16 is detachable with a measuring member mounting section 18 of an SPFS measurement apparatus 10, and the sensor chip 16 is mounted thereon for use at the start of the measurement.

In the embodiment shown in FIG. 2A, the substrate-form member 16a comprises: the prism-shaped dielectric member 12 for introducing an excitation light to the backside of the metal thin film 14, which dielectric member 12 has a substantially trapezoidal vertical cross-sectional shape; the metal thin film 14 for generating surface plasmon resonance, which is formed on a horizontal upper surface 12a of the dielectric member 12; and a reaction layer which is formed on an upper surface 14a of the metal thin film 14 and contains a capturing substance immobilized for capturing the substance to be detected on the surface of the metal thin film 14. As required, the substrate-form member 16a may further comprise a spacer layer for inhibiting metal quenching of fluorescence caused by excessive proximity of a phosphor to the metal thin film, which spacer layer is formed between the metal thin film 14 and the reaction layer.

In the embodiment shown in FIG. 2B, the substrate-form member 16a is different from that of the embodiment shown in FIG. 2A in that it adopts a constitution in which the prism-shaped dielectric member 12 and a transparent planar substrate 13, which is made of the same material as the dielectric member 12, are separated. The metal thin film 14 is not formed on the dielectric member 12 but on the surface of the transparent planar substrate 13, and the reaction layer and the spacer layer, which are arranged as required, are formed on the metal thin film 14. In this case, the dielectric member 12 is fixedly installed in the measurement apparatus 10 (on the measuring member mounting section 18) to constitute a part of the measurement apparatus 10. Meanwhile, the substrate-form member 16a comprising the transparent planar substrate 13 and the like is joined with the flow channel member 16b to form the sensor chip 16, which is subsequently mounted on the measurement apparatus 10 (measuring member mounting section 18) for use. As a result, the other side (backside) of the transparent planar substrate 13 is arranged such that it is tightly adhered with the upper surface 12a of the dielectric member 12, and measurement can be carried out in the same manner as in the embodiment shown in FIG. 2A.

The part where the reaction layer is formed on the metal thin film corresponds to the measurement region 38. The measurement region 38 may be arranged by forming the reaction layer on the entire bottom surface of the flow channel 36 (or well), or by forming the reaction layer only on a portion of the bottom surface, in a desired pattern as required. The area of the measurement region 38 can be adjusted taking into consideration the irradiation area of an incoming light 22 (excitation light) that is irradiated generally as a laser light. For example, when the spot diameter of the incoming light 22 is about 1 mmφ, the measurement region 38 is usually designed in such a manner to have an area of at least several millimeters square.

When the SPFS system is of a "flow channel-type" in which various solutions are transferred through the flow channel 36 as shown in FIGS. 2 and 3, the flow channel member 16b for forming the flow channel can be constructed using, for example, a film-form "flow cell" which forms the wall of the flow channel and has holes and a "top plate" having a liquid inlet port and a liquid outlet port at the positions corresponding to the holes of the flow cell, and the flow channel 36 can be formed by tightly adhering and fixing the flow cell and the top plate on the substrate-form member 16a. The sensor chip surface at the positions corresponding to the holes of the flow cell constitutes the bottom surface of the flow channel 36, and the measurement region 38 is formed thereon. Alternatively, the flow channel 36 can also be constructed by disposing a member, which is used as the flow channel member 16b and on which a groove is formed with a depth corresponding to the height of the flow channel and through-holes corresponding to a liquid inlet port and a liquid outlet port are arranged at the respective ends of the groove, in a tightly adhered and fixed manner with the groove being arranged inside.

In the case of such a flow channel-type SPFS system, for example, by using a liquid transfer means including a pump and a tube, various liquids can be introduced to the flow channel via the liquid inlet port and discharged from the liquid outlet port and, as required, the liquids can be transferred in a reciprocating manner or a circulating manner. The conditions such as the liquid transfer rate and the liquid transfer (circulation) time can be adjusted as appropriate while taking into consideration the sample amount, the concentration of the substance to be detected in the sample, the size of the flow channel or well, the mode of the reaction layer (e.g., the density of the capturing substance), the pump performance and the like.

Meanwhile, the SPFS system may be of a "well-type" in which various solutions are retained in a space larger than the above-described flow channel. In that case, a "well member" having through-holes for forming a well can be mounted and fixed on the substrate-form member 16a in place of the above-described flow channel member 16b. In such a well-type SPFS system, for example, various liquids can be added to and removed from the well using a pipet-like member or the like.

The flow cell can be made of, for example, a sheet-form polydimethylsiloxane (PDMS). The top plate is prepared from a transparent material so that the fluorescence emitted from the measurement region 38 can be measured, and the top plate can be made of, for example, a plate-form polymethylmethacrylate (PMMA). Alternatively, the flow cell and the top plate can each be made of a plastic that is molded or photolithographed into a desired shape.

The means for tightly adhering and fixing the flow cell or well member on the substrate-form member 16a is not particularly restricted, and these processes can be generally performed by physical application of pressure from both the top and the bottom and, if necessary, an adhesive, a matching oil, a transparent adhesive sheet or the like that has the same photorefractive index as that of the transparent support may also be used.

The SPFS measurement apparatus 10 basically comprises, for example: measuring member mounting section 18 with which an SPFS measuring member is detachable; a light source 20 for irradiating an excitation light (preferably a laser light) having a wavelength appropriate for the phosphor to be used; a light-receiving means 26 (a light receiver and a moving means) which receives light reflected by the metal thin film and measures the intensity thereof; a lens for condensing fluorescence emitted from the phosphor; a light-detecting means 32 (e.g., a detector) for measuring the intensity of the fluorescence; various filters (not shown) for allowing only the excitation light and fluorescence that has a prescribed wavelength to transmit therethrough and cutting other light; and a liquid transfer means (not shown) for supplying various solutions to the flow channel or well of the SPFS measuring member.

As shown in the figure, the light source 20 is arranged inferiorly to the dielectric member 12 on the side of a side surface 12b. The light source 20 may be any light source as long as it is capable of irradiating an excitation light that corresponds to the fluorescent dye of the labeled lectin and, for example, a laser diode (LD) can be used as the light source 20. The light source 20 is equipped with an incidence angle-adjusting means (not shown) which is capable of appropriately altering an incidence angle α1 of the incoming light 22 with respect to the metal thin film 14. The incoming light 22 enters the dielectric member 12 through the side surface 12b from below and can be irradiated via the dielectric member 12 toward the metal thin film 14 at an incidence angle suitable for maximizing surface plasmon resonance. Further, between the light source 20 and the dielectric member 12 (side surface 12b), a polarization filter, which is used for P-polarization of the incoming light 22 (laser light) irradiated from the light source 20 so as to allow surface plasmon to be efficiently generated on the metal thin film 14, may also be arranged.

Inferiorly to the dielectric member 12 and on the side of the other side surface 12c, the light-receiving means 26, which receives a reflected light 24 that is the incoming light 22 reflected by the metal thin film 14, is arranged. When an evanescent wave is generated on the side of the upper surface 14a of the metal thin film 14 and surface plasmon resonance is thereby induced and enhanced, the reflected light 24 is attenuated more than the incoming light 22 in accordance with the extent of the surface plasmon resonance; therefore, whether or not the incidence angle α1 is appropriate can be determined based on the amount of light measured by the light-receiving means 26. The light-receiving means 26 is also equipped with a moving means (not shown) and capable of surely receiving the reflected light 24 in synchronization with the incidence angle-adjusting means of the light source 20 even when the incidence angle α1 and the reflection angle are changed.

A photodetector is positioned above the measurement region 38 such that the light-detecting means 32 can measure the fluorescence emitted from the measurement region 38 of the sensor chip 16. As the photodetector, for example, a photomultiplier tube (PMT) can be used. Further, the light-detecting means 32 is also usually equipped with a condenser lens, or a filter for condensation of only the fluorescence having a specific wavelength and elimination of other fluorescence.

The light-receiving means 26 and the light-detecting means 32 are each connected to a control calculation means 40 and configured in such a manner that the amount of the reflected light 24 received by the light-receiving means 26 and the amount of fluorescence 30 received by the light-detecting means 32 are transmitted to and processed by the control calculation means 40. For example, they can be configured in such a manner that the S/B ratio can be automatically calculated based on the data of the amount of the fluorescence 30 measured in a prescribed step. Further, the control calculation means 40 may also be imparted with a function of appropriately operating a constituting member (s) of the SPFS measurement apparatus 10 in accordance with a prescribed program.

It is noted here that a unit constituted by the sensor chip 16, the light source 20 and the light-detecting means 32 may be referred to as "SPFS measurement section 34" which performs fluorescence measurement based on SPFS. Further, a unit constituted by the sensor chip 16, the light source 20 and the light-receiving means 26 may be referred to as "SPR measurement section 28".

<Application of Sandwich Assay>

The sandwich assay of the present invention can be utilized in a variety of applications where it is required to quantify a substance to be detected, and the purpose of the utilization is not particularly restricted.

One example of a preferred application of the sandwich assay of the present invention is where a glycoprotein that serves as a marker of a disease is quantified by the sandwich assay as a substance to be detected and the measurement results are used for the diagnosis of the disease. As described above, by the sandwich assay of the present invention performed in accordance with SPFS or the like, noise is markedly reduced and a signal and S/B ratio that more accurately represent the amount of the substance to be detected can be obtained. The use of such data enables to more accurately diagnose whether or not a subject who provided the sample is a patient of the particular disease. For example, in a method of diagnosing whether or not a subject has prostate cancer (whether the subject has prostatic hyperplasia or is healthy) based on the blood concentration of a PSA having a LacdiNAc residue-containing sugar chain (specific PSA), by measuring the blood concentration of the specific PSA by performing the sandwich assay of the present invention in accordance with SPFS, an abnormal increase in measured values caused by noise originating from a contaminant can be suppressed, so that the risk of falsely diagnosing the subject with prostate cancer when the subject does not actually have prostate cancer can be reduced, that is, the specificity for prostate cancer can be improved.

—Kit—

The kit of the present invention is a kit which can perform a sandwich assay for quantification of a glycoprotein as a substance to be detected using a labeled lectin and a capturing substance immobilized on a measurement region, wherein the kit comprises at least a substance showing an action of cleaving disulfide bonds (S—S bond-cleaving agent) for a treatment of a glycoprotein that is a contaminant. Such a kit of the present invention is suitable for efficiently performing the sandwich assay of the present invention which comprises the above-described cleavage treatment.

In addition to the S—S bond-cleaving agent such as a reducing agent, the kit of the present invention may also contain a reagent (s) and/or an instrument (s) that are used for performing the sandwich assay of the present invention. For example, when the kit is configured for performing an SPFS-based sandwich assay, the kit may contain at least one selected from, preferably all of, for example: a substrate-form member (a dielectric member or a transparent planar substrate) which comprises a reaction layer containing an immobilized capturing substance (e.g., an antibody) and the like; a flow channel member (a flow cell or a top plate) or a well member; a sample diluent; a labeled lectin; a washing liquid; a fluorimetric liquid; and a reagent container in which a solution of these liquids is stored and tightly sealed in advance and which can be mounted on an SPFS apparatus. In place of the substrate-form member which comprises a reaction layer and the like, the kit may contain, for the preparation of the substrate-form member: an unmodified substrate-form member; a capturing substance (e.g., an antibody); as required, for immobilization of a capturing substance on the surface of a metal thin film, a silane coupling agent, a SAM, a hydrophilic polymer such as carboxymethyldextran and a reaction reagent; and a preparation equipment(s). In place of the labeled lectin, the kit may contain, for the preparation of the labeled lectin: a lectin; a label such as a fluorescent dye; a reaction reagent and a solvent for linking the lectin and the label; and a preparation equipment (s). In place of the washing liquid, the kit may contain, for the preparation of the washing liquid: a cleaning agent; a solvent; and a preparation equipment (s). Further, the kit of the present invention may also contain an instruction manual that describes the procedures for performing the sandwich assay of the present invention.

In a preferred embodiment, the kit of the present invention contains a labeled lectin prepared from *Wisteria floribunda* lectin (WFA), soybean lectin (SBA), *Trichosanthes japonica* lectin-II (TJA-II) or *Vicia sativa* lectin (VVL), which primarily binds to a LacdiNAc residue as described above.

Further, it is preferred to prepare a solution of an S—S bond-cleaving agent in advance and use it as a sample diluent because this enables to efficiently treat a contaminant contained in a sample in, for example, embodiments that are carried out in accordance with the above-described treatment orders (1) to (4). Accordingly, it is preferred that the kit of the present invention contain an S—S bond-cleaving agent along with a sample diluent in which the S—S bond-cleaving agent can be dissolved, or a sample diluent in which an S—S bond-cleaving agent has already been dissolved in advance.

EXAMPLES

Preparation Example 1: SPFS Measurement Apparatus

An SPFS measurement apparatus having the constitution shown in FIGS. 2B and 3B was prepared (it is noted here that the symbols used in the following descriptions are the same as in FIGS. 2B and 3B). Further, using a 60° prism manufactured by Sigmakoki Co., Ltd. as a dielectric member 12, a sensor chip 16, which was prepared using a transparent planar substrate 13 obtained by the below-described Preparation Example 2 and had a flow channel 36 in which an anti-PSA antibody was immobilized on a measurement region 38, was fixed on the upper surface of the dielectric member 12. As a light source 20, a laser diode (LD) capable of irradiating a light having a wavelength of 635 nm was used. Between the light source 20 and the dielectric member 12, a light attenuation filter (neutral density filter) was arranged as an optical filter so that the photon amount could be adjusted. Above the measurement region 38 of the sensor chip 16, an objective lens was arranged as a condenser lens, and a photomultiplier tube (PMT) was further installed as a photodetector and used as a light-detecting means 32.

Preparation Example 2: SPFS Measuring Member

After plasma-cleaning a 1 mm-thick glass transparent planar substrate having a refractive index of 1.72, "S-LAL 10" (manufactured by Ohara Inc.), a chromium thin film was formed on one side of this substrate by sputtering. Then, a gold thin film was further formed on the surface of this chromium thin film by sputtering. The chromium thin film had a thickness of 1 to 3 nm and the gold thin film had a thickness of 44 to 52 nm.

The substrate having the gold thin film formed in this manner was immersed in an ethanol solution containing 1 mM of 10-carboxy-1-decanethiol for at least 24 hours to form a SAM film (Self-Assembled Monolayer) composed of the molecules thereof on the surface of the gold thin film. The substrate was then removed from the solution and washed with ethanol and isopropanol, after which the substrate was dried using an air gun.

On this substrate, 0.8 mL of 25 mM MES-buffered physiological saline and 10 mM NaCl solution (pH 6.0), which 25 mM MES-buffered physiological saline contained 0.5 mM of N-hydroxysuccinimide (NHS), 0.5 mM of water-soluble carbodiimide (WSC) and 1 mg/mL of carboxymethyldextran "CMD-500-06I4" (manufactured by Meito Sangyo Co., Ltd.: average molecular weight=500,000, degree of substitution=0.51), was applied dropwise and allowed to react for 20 minutes, whereby a film composed of carboxymethyldextran (CMD film) was formed on the SAM.

Then, a polydimethylsiloxane (PDMS) sheet having a groove of 0.5 mm in height as a flow channel and a through-hole at each end of the groove was disposed on the substrate with the groove facing the CMD film such that the surface of the CMD film was arranged inside the flow channel. The PDMS sheet outside the flow channel was press-adhered from above, and the PDMS sheet (flow channel 36) was screw-fixed with a plasmon excitation sensor.

A peristaltic pump was connected to the flow channel that was constructed on the plasmon excitation sensor in the above-described manner, and ultrapure water and then phosphate-buffered physiological saline (PBS) were circulated in the flow channel for 10 minutes and 20 minutes, respectively, at room temperature (25° C.) and a flow rate of 500 μL/min, whereby the surface of the plasmon excitation sensor was equilibrated.

Subsequently, 5 mL of a PBS solution containing 50 mM of N-hydroxysuccinimide (NHS) and 100 mM of water-soluble carbodiimide (WSC) was introduced to the flow channel and circulated therein for 20 minutes at a flow rate of 500 μL/min to convert the carboxyl group of CMD into an active ester. Thereafter, 2.5 mL of an anti-PSA monoclonal antibody solution (No. 72, 2.5 mg/mL; manufactured by Mikuri Immunolaboratory, Ltd.) was circulated for 30 minutes at a flow rate of 500 μL/min so as to allow the antibody to bind with the active ester group of CMD, whereby the anti-PSA monoclonal antibody was immobilized on the SAM film and a measurement region was constructed.

Lastly, a PBS solution containing 1 wt % of bovine serum albumin (BSA) was circulated for 30 minutes at a flow rate of 500 μL/min to perform a non-specific adsorption-inhibiting treatment (blocking treatment) in the flow channel.

Preparation Example 3: Fluorescently Labeled Lectin

A fluorescently labeled lectin (Alexa Fluor 647-labeled WFA) was prepared using a fluorescent substance labeling kit, "Alexa Fluor (registered trademark) 647 Protein Labeling Kit" (manufactured by Invitrogen Corp.). After mixing 100 μg equivalent of WFA lectin (*Wisteria floribunda* lectin) "L-1350" (manufactured by Vector Laboratories, Inc.), 0.1 M sodium bicarbonate and an Alexa Fluor 647-reactive dye and allowing them to react at room temperature for 1 hour, the resultant was subjected to gel filtration chromatography and ultrafiltration, whereby the Alexa Fluor 647-reactive dye that was not utilized for labeling was removed and a fluorescently labeled WFA was recovered. The absorbance of the thus obtained fluorescently labeled WFA solution was measured to quantify its concentration, and this solution was diluted with PBS to adjust the concentration at 1 μg/mL.

Preparation Example 4: Sample for Signal Acquisition and Sample for Background Acquisition As a positive sample, a serum sample was prepared by adding LNCaP (human prostate cancer cell line) culture supernatant to PSA-free pooled serum (normal human pooled serum, manufactured by Kohjin Bio Co., Ltd.; the PSA concentration was verified to be 0.01 ng/mL or lower by ELISA) to a total PSA concentration of 2 ng/mL, and this serum sample was used as a sample for signal (S) acquisition.

Further, from the PSA-free pooled serum, a serum sample solution having a PSA concentration of 1 pg/mL (0.001 ng/mL) or lower as determined by ELISA and showing a non-specific reaction was selected and used as a sample for background (B) acquisition.

[Example 1] Case where Sodium Metabisulfite was Used as Reducing Agent (Measurement of Signal Value)

A PBS solution (pH 7.4) containing 3.5 wt % of sodium metabisulfite as a reducing agent was prepared and used as a treatment solution. Then, 100 μL of this treatment solution was added to 50 μL of the sample for signal acquisition, and the resultant was thoroughly stirred in a test tube and left to stand at room temperature for 5 minutes.

Subsequently, 100 μL of the thus treated sample for signal acquisition was introduced to the flow channel of an SPFS measuring member, which was installed on the SPFS measurement apparatus, and circulated therein for 30 minutes at a flow rate of 200 μL/min, whereby the sample was allowed to react with the measurement region. Then, a TBS (TBS-T) solution containing 0.05 wt % of "Tween (registered trademark) 20" was introduced to the flow channel and circulated therein for 3 minutes to wash the flow channel and the measurement region.

Next, 100 μL of the fluorescently labeled lectin (Alexa Fluor 647-labeled WFA) solution having a concentration of 1 μg/mL, which was prepared in Preparation Example 3, was introduced to the flow channel and circulated therein for 10 minutes at a flow rate of 200 μL/min, whereby the solution was allowed to react with the measurement region. Then, a TBS (TBS-T) solution containing 0.05 wt % of "Tween (registered trademark) 20" was introduced to the flow channel and circulated therein for 3 minutes to wash the flow channel and the measurement region. Thereafter, with the flow channel being filled with this TBS solution, an excitation light was irradiated thereto and the intensity of fluorescence emitted by Alexa Fluor 647 was measured, and the thus obtained value was defined as signal value.

(Measurement of Background Value)

The intensity of fluorescence emitted by Alexa Fluor 647 was measured by the same procedure as the above-described "Measurement of Signal Value" except that the sample for background acquisition was used in place of the sample for signal acquisition, and the thus obtained value was defined as background value.

(Calculation of S/B Ratio)

The S/B ratio, which is the ratio of the signal value acquired by the above-described procedure with respect to the background value obtained by the above-described procedure, was calculated.

[Example 2] Case where Thioglycerol was Used as Reducing Agent

Signal value and background value were obtained and the S/B ratio was calculated by the same procedures as in Example 1, except that a treatment solution in which thioglycerol was added in place of sodium metabisulfite was used.

[Example 3] Case where Sodium Toluenethiosulfinate was Used as Reducing Agent

Signal value and background value were obtained and the S/B ratio was calculated by the same procedures as in Example 1, except that a treatment solution in which sodium toluenethiosulfinate was added in place of sodium metabisulfite was used.

[Comparative Example 1] Case where No Reducing Agent was Used

Signal value and background value were obtained and the S/B ratio was calculated by the same procedures as in Example 1, except that a treatment solution with no addition of sodium metabisulfite was used.

<Results>

The results of Examples 1 to 3 and Comparative Example are shown in Table 1 and FIG. 4. The signal values shown in Table 1 are actual values (S), each corresponding to a sum of the signal value originated from the specific PSA and the signal value originated from the background (B).

As compared to the case where no reducing agent was used (Comparative Example), the background value reflecting the amount of non-specifically adsorbed and WFA-reactive contaminant was markedly reduced when a reducing agent was used (Examples 1 to 3), and it is thus seen that the reducing agents showed a prominent effect of diminishing such non-specifically adsorbed substance. Meanwhile, the use of a reducing agent also resulted in a decrease in the signal value reflecting the amount of the substance to be detected (LacdiNAc-PSA), and it is thus seen that the reducing agents also had some effect on the substance to be detected. Yet, since the effect of lowering the background value was greater as a whole, the S/B ratio was markedly improved. Accordingly, while samples that are derived from patients and contain a large amount of LacdiNAc-PSA result in the detection of a high S/B ratio, samples that are derived from healthy individuals and contain hardly any LacdiNAc-PSA result in the detection of a low S/B ratio (in this case, the S/B ratio is close to 1 since S and B are almost the same); therefore, the specificity and sensitivity for samples derived from patients are improved and the possibility of falsely diagnosing a healthy individual as a patient can thereby be reduced.

TABLE 1

| Example/Comparative Example | Composition of treatment solution | Background value (B) | Signal value (S) | S/B ratio |
|---|---|---|---|---|
| Comparative Example 1 | PBS(—), pH 7.4 | 40,000 | 269,700 | 6.7 |
| Example 1 | 3.5-wt % sodium metabisulfite-containing PBS(—), pH 7.4 | 700 | 130,450 | 186.4 |

TABLE 1-continued

| Example/Comparative Example | Composition of treatment solution | Background value (B) | Signal value (S) | S/B ratio |
|---|---|---|---|---|
| Example 2 | 3.5% thioglycerol-containing PBS(—), pH 7.4 | 1,600 | 176,350 | 110.2 |
| Example 3 | 3.5% sodium toluenethiosulfinate-containing PBS(—), pH 7.4 | 5,350 | 96,300 | 18.0 |

[Reference Example 1] Examination of Contaminants as Factors for Abnormally High Values in Healthy Individuals For 35 samples derived from prostate cancer patients, 30 samples derived from prostatic hyperplasia patients (prostatic hyperplasia samples) and 25 samples derived from healthy individuals (healthy individual samples), the SPFS signal value was determined in the same manner as in Comparative Example 1 where no reducing agent was used. The results thereof are shown in FIG. 5 (left). Next, for those prostatic hyperplasia samples and healthy individual samples that had a high SPFS signal value, the total PSA amount was quantified in accordance with ELISA method. The results thereof are shown in FIG. 5 (right). Comparing the data in the rectangular box of FIG. 5 (left) for the results of prostatic hyperplasia samples and healthy individual samples, it is seen that, despite the healthy individual samples had a lower total PSA content than the prostatic hyperplasia samples, the healthy individual samples showed increased SPFS signal values used for the measurement of the specific sugar chain-containing PSA (LacdiNAc-PSA).

In order to determine the cause thereof, the healthy individual samples were treated with a WFA column and the electrophoresis analysis was performed for the bound fractions. The results thereof are shown in FIG. 6. In order to specify the substance represented by each band, after a trypsin treatment, an identification test by MALDI-TOF-MS (matrix-assisted laser desorption ionization) was performed. As a result, five candidate substances: inter-α-trypsin inhibitor (IαI), α2-macroglobulin (α2M), haptoglobin (HP), immunoglobulin M (IgM) and immunoglobulin G (IgG) emerged.

These five candidates are all common serum proteins and their standard reagents are commercially available. The standard reagents were treated with sialidase and then added to a PBS buffer, followed by measurement of the SPFS signal. The results thereof are shown in FIG. 7. In the healthy individual samples that were used this time, a prominently high SPFS signal value that could be a noise was confirmed for IgM. In addition, SPFS signals that could be a noise were also confirmed for IαI, α2M, HP and IgG, although they were weaker than that of IgM.

In order to further examine IgM, the healthy individual samples were each treated with an IgM purification column and the SPFS signal was measured for each sample before the column treatment, for flow-through fractions (IgM-removed fractions) and for bound fractions (fractions with elution of IgM). The results thereof are shown in FIG. 8. For all of the healthy individual samples, the measured signal was largely reduced in the flow-through fractions, while it was high in the bound fractions. Therefore, it was shown that non-specific adsorption of IgM is the factor for the increase in the signal values in the healthy individual samples as described above at the beginning; and that it is extremely probable that the background can be markedly reduced by eliminating the non-specific adsorption of IgM.

DESCRIPTION OF SYMBOLS

10: SPFS measurement apparatus
12: Dielectric member
12a: Upper surface
12b: Side surface
12c: Side surface
13: Transparent planar substrate
14: Metal thin film
14a: Upper surface
16: Sensor chip
16a: Substrate-form member
16b: Flow channel member
18: Measuring member mounting section
20: Light source
22: Incoming light
24: Reflected light
26: Light-receiving means
28: SPR measurement section
30: Fluorescence
32: Light-detecting means
34: SPFS measurement section
36: Flow channel
38: Measurement region
40: Quantitative calculation means
50: Capturing substance
52: Labeled lectin
52a: Fluorescent substance
54: Support
60: Substance to be detected
60a: Sugar chain
62: Contaminant
62a: Sugar chain
62b: Domain (fragmented contaminant)

The invention claimed is:
1. A sandwich assay for quantifying a glycoprotein as a substance to be detected, using a labeled lectin and a capturing substance immobilized on a measurement region, said sandwich assay comprising a treatment for inhibiting the binding of said labeled lectin to a sugar chain that is carried by a contaminant non-specifically adsorbed to said measurement region and is the same as that of said substance to be detected,
wherein said treatment for inhibiting the binding of said labeled lectin to said sugar chain is a treatment of bringing a substance showing an action of cleaving disulfide bonds into contact with said contaminant and thereby dissociating a domain comprising said same sugar chain as that of said substance to be detected,
said substance showing an action of cleaving disulfide bonds is brought into contact with said contaminant before said contaminant is brought into contact with said capturing substance, said substance to be detected is a glycoprotein comprising an N-acetyl-D-galactosamine β1-4 N-acetylglucosamine residue-containing sugar chain, and said substance showing an action of cleaving disulfide bonds is at least one selected from the group consisting of sodium metabisulfite and sodium toluenethiosulfinate.

2. The sandwich assay according to claim 1, wherein
said contaminant non-specifically adsorbed to said measurement region is a glycoprotein comprising the same sugar chain as said substance to be detected.

3. The sandwich assay according to claim 2, wherein said substance to be detected is a glycoprotein which comprises: the same sugar chain as that of said glycoprotein as said contaminant; and a binding site for said capturing substance, within the same domain.

4. The sandwich assay according to claim 2, wherein
said contaminant comprises an N-acetyl-D-galactosamine β1-4 N-acetylglucosamine residue-containing sugar chain, and said labeled lectin is *Wisteria floribunda* lectin (WFA), soybean lectin (SBA), *Trichosanthes japonica* lectin-II (TJA-II) or *Vicia sativa* lectin (VVL) that is labeled.

5. The sandwich assay according to claim 2, wherein said contaminant is at least one selected from the group consisting of immunoglobulin M (IgM), inter-α-trypsin inhibitor (IαI), α2-macroglobulin (α2M), haptoglobin (HP) and immunoglobulin G (IgG).

* * * * *